United States Patent [19]
Balaji et al.

[11] Patent Number: 5,736,509
[45] Date of Patent: Apr. 7, 1998

[54] CYCLIC PEPTIDE SURFACE FEATURE MIMICS OF ENDOTHELIN

[75] Inventors: Vitukudi Narayanaiyengar Balaji, Encinitas; Ming Fai Chan, San Diego, both of Calif.

[73] Assignee: Texas Biotechnology Corporation, Houston, Tex.

[21] Appl. No.: 410,955

[22] Filed: Nov. 10, 1994

Related U.S. Application Data

[63] Continuation-in-part of Ser. No. 223,513, Apr. 5, 1994, and a continuation-in-part of Ser. No. 900,623, Jun. 18, 1992, abandoned, which is a continuation-in-part of Ser. No. 628,111, Dec. 14, 1990, Pat. No. 5,331,573.

[51] Int. Cl.$^6$ .............................. A61K 38/00; C07K 5/00
[52] U.S. Cl. .................. 514/9; 514/17; 530/317; 530/330; 930/270
[58] Field of Search ............... 514/9, 17; 530/317, 530/330; 930/270

[56] References Cited

U.S. PATENT DOCUMENTS

| | | | |
|---|---|---|---|
| 3,300,488 | 1/1967 | Onoue et al. | 260/239.9 |
| 3,660,383 | 5/1972 | Sumimoto et al. | 260/239.9 |
| 4,044,126 | 8/1977 | Cook et al. | 424/243 |
| 4,364,923 | 12/1982 | Cook et al. | 424/46 |
| 4,414,209 | 11/1983 | Cook et al. | 424/243 |
| 4,522,811 | 6/1985 | Eppstein et al. | 514/2 |
| 4,752,613 | 6/1988 | Floyd et al. | 514/438 |
| 4,852,017 | 7/1989 | Hunkapiller | 364/497 |
| 4,853,871 | 8/1989 | Pantoliano et al. | 364/496 |
| 4,881,175 | 11/1989 | Ladner | 364/496 |
| 4,908,773 | 3/1990 | Pantoliano et al. | 364/496 |
| 4,939,666 | 7/1990 | Hardman | 364/496 |
| 4,997,836 | 3/1991 | Sugihara et al. | 514/253 |
| 5,081,584 | 1/1992 | Ominchinski et al. | 364/497 |
| 5,082,838 | 1/1992 | Naka et al. | 514/211 |
| 5,114,918 | 5/1992 | Ishikawa et al. | 514/11 |
| 5,187,195 | 2/1993 | Oohata et al. | 514/510 |
| 5,198,548 | 3/1993 | Beylin et al. | 546/136 |
| 5,208,243 | 5/1993 | Peglion et al. | 514/309 |
| 5,230,999 | 7/1993 | Suzuki et al. | 435/71 |
| 5,240,910 | 8/1993 | Lam et al. | 514/11 |
| 5,248,807 | 9/1993 | Fujimoto et al. | 560/75 |
| 5,260,276 | 11/1993 | Cody et al. | 514/14 |
| 5,270,313 | 12/1993 | Burri et al. | 514/252 |
| 5,292,740 | 3/1994 | Burri et al. | 514/256 |
| 5,334,598 | 8/1994 | Bagley et al. | 514/303 |
| 5,352,659 | 10/1994 | Wakimasu et al. | 514/9 |
| 5,352,800 | 10/1994 | Bills et al. | 548/539 |
| 5,378,715 | 1/1995 | Stein et al. | 514/329 |
| 5,389,620 | 2/1995 | Ishikawa et al. | 514/80 |
| 5,389,633 | 2/1995 | Miyake et al. | 514/233.2 |
| 5,444,152 | 8/1995 | Ishikawa et al. | 530/331 |
| 5,492,892 | 2/1996 | Anderson et al. | 514/13 |
| 5,585,397 | 12/1996 | Tung et al. | 514/473 |
| 5,589,478 | 12/1996 | Yamada et al. | 514/269 |

FOREIGN PATENT DOCUMENTS

| | | |
|---|---|---|
| 2067288 | 10/1992 | Canada. |
| 2071193 | 12/1992 | Canada. |
| 0177163 | 8/1985 | European Pat. Off.. |
| 0404525 | 12/1990 | European Pat. Off.. |
| 0405421 | 1/1991 | European Pat. Off.. |
| 0411150 | 2/1991 | European Pat. Off.. |
| 0436189 | 7/1991 | European Pat. Off.. |
| 0457195 | 11/1991 | European Pat. Off.. |
| 0460679 | 12/1991 | European Pat. Off.. |
| 0496452 | 1/1992 | European Pat. Off.. |
| 0558258 | 2/1993 | European Pat. Off.. |
| 0569193 | 4/1993 | European Pat. Off.. |
| 2259450 | 9/1991 | United Kingdom. |
| 9308799 | 10/1992 | WIPO. |
| 9403483 | 2/1994 | WIPO. |
| 9524385 | 9/1995 | WIPO. |

OTHER PUBLICATIONS

Science vol. 256 24 Apr. 1992 pp. 440–442.
Arai, et al., "Cloning and expression of a cDNA encoding an endothelin receptor," *Nature*, 348:730–732 (1990).
Benigni, et al., "A specific endothelin subtype A receptor antagonist protects against injury in renal disease progression," *Kidney International*, 44:440–444 (1993).

(List continued on next page.)

*Primary Examiner*—Cecilia J. Tsang
*Assistant Examiner*—Bennett Celsa
*Attorney, Agent, or Firm*—Stephanie L. Seidman; Brown Martin Haller & McClain

[57] ABSTRACT

Cyclic peptides and pharmaceutically acceptable salts and esters thereof are provided. The cyclic peptides and pharmaceutically acceptable salts and esters thereof mimic surface features of the C-terminus of endothelin and thereby can be used modulate or alter the activity of the endothelin family of peptides. More particularly, cyclic pentapeptides, cyclic hexapeptides, cyclic heptapeptides and pharmaceutically acceptable derivatives of the peptides that specifically inhibit the activity of endothelin are provided. Among the cyclic peptides are those that have the formula: cyclo($X^1$-$X^2$-$X^3$-$X^4$-D-Trp): $X^1$ is D-Tyr or D-Asp; $X^2$ is Phe, Ala, $Ac_3c$ or Pro; $X^3$ is D-His, D-Ala, D-Val, Gly or β-Ala; and $X^4$ is His, Ala, β-Ala, Aib, Gly, D-His-gly or Leu; cyclo ($X^1$-L-Phe-$X^3$-$X^4$-$X^5$) in which $X^1$ is D-Tyr, D-Asp or D-Glu, $X^3$ is selected from among D-His, β-Ala-D-His or gly-D-His; $X^4$ is Ser, Gly or β-Ala, and $X^5$ is D-Trp or N-Me-D-Trp; cyclo($X^1$-$X^2$-$X^3$-$X^4$-L-Trp) in which $X^1$ is D-Ala, Aib, Gly, D-Val, D-Leu, D-Ile, D-Nva, D-Nle, or D-Alle; $X^2$ is D-Val, D-Leu, D-Ile, D-Ala, D-Gln, Gly, Aib, D-Nva, D-Nle, or D-Alle; $X^3$ is Pro, Gly, Aib, Val, Leu, L-Nva, L-Nle, L-Alle or L-Hyp and $X^4$ is D-Asp, D-Glu, D-Ser, D-Thr, D-Tyr, D-Cys($O_3$H) or D-Pen($O_3$H); and cyclo($X^1$-$X^2$-$X^3$-$X^4$-L-Trp) in which $X^1$ is D-Leu, D-Val, D-Ile, D-Ala, Gly, Aib, D-Nva, D-Nle or D-Alle; $X^2$ is Val, Ile, Leu, Ala, Gln, Gly, Aib, L-Nva, L-Nle or L-Alle; $X^3$ is D-Pro, D-Hyp, D-Ala, D-Val, D-Ile, Gly, Aib, D-Nva, D-Nle or D-Alle; and $X^4$ is Asp, Glu, Tyr, Ser, Thr, L-Cys($O_3$H) or L-Pen($O_3$H). Pharmaceutical compositions containing the peptides and methods of modulating the activity of endothelin peptides are also provided.

41 Claims, 6 Drawing Sheets

OTHER PUBLICATIONS

Clozel, et al., "Pathophysiological role of endothelin revealed by the first orally active endothelin receptor antagonist," Nature, 365:759–761 (1993).

Cody, et al., "The rational design of a highly potent combined $ET_A$ and $ET_B$ receptor antagonist (PD 145065) and related analogues," Med. Chem. Res., 3:154–162 (1993).

de Castiglione, et al., "Alanine scan of endothelin," Peptides: Chemistry and Biology, Proc. Amer. Pept. Symp. (Twelfth) [J.A. Smith and J.E. Rivier, Eds.] ESCOM, Leiden, pp. 402–403 (1992).

de Nucci, et al., "Pressor effects of circulating endothelin are limited by its removal in the pulmonary circulation and by the release of prostacyclin and endothelin–derived relaxing factor," Proc. Natl. Acad. Sci. USA, 85:9797–9800 (1988).

Fujimoto, et al., "A novel non–peptide endothelin antagonist isolated from bayberry, Myrica cerifera," FEBS Letters, 305(1):41–44 (1992).

Ishikawa et al., "Cyclic pentapeptide endothelin antagonists with high $ET_A$ selectivity. Potency and solubility–enhancing modifications," J. Med. Chem., 35:2139–2142 (1992).

Ishikawa, et al., "Endothelin antanogistic cyclic pentapeptides with high selectivy for $ET_A$ receptor," Peptides: Chemistry and Biology, Proc. Amer. Pept. Symp. (Twelfth) [J.A. Smith and J.E. Rivier, Eds.] ESCOM, Leiden, pp. 812–813 (1992).

Kaltenbronn, et al., "Renin inhibitors containing isoteric replacements of the amide bond connecting the $P^3$ and $P^2$ sites," J. Med. Chem., 33:838–845 (1990).

Kimura, et al., "Structure–activity relationship of endothelin: Importance of the C–terminal moiety," Biochem. and Biophys. Res. Comm., 156(3):1182–1186 (1988).

Kloog and Sokolovsky, "Similarities in mode and sites of action of sarafotoxins and endothelins," TIPS, 10:212–214, date is not available.

Maggi, et al., "Potent contractile effect of endothelin in isolated guinea–pig airways," Eur. J. of Pharm., 160:179–182 (1989).

Martin, et al., "Identification and characterization of endothelin binding sites in rat renal papillary and glomerular membranes," Biochem. and Biophys. Res. Comm., 162(1):130–137 (1989).

Miyata, et al., "WS–7338, new endothelin receptor antagonists isolated from Streptomyces sp. No. 7338 I. Taxonomy, fermentation, isolation, physico–chemical properties and biological activities," J. Antibiotics, 45(1):74–82 (1992).

Miyata et al., "WS009 A and B, new endothelin receptor antagonists isolated from Streptomyces sp. No. 89009 I. Taxonomy, fermentation, isolation, physico–chemical properties and biological activities," J. Antibiotics, 45(7):1029–1040 (1992).

Miyata et al., "WS009 A and B, new endothelin receptor antagonists isolated from Streptomyces sp. No. 89009 II. Biological characterization and pharmacological characterization of WS009 A and B," J. Antibiotics, 47(7):1041–1046 (1992).

Morel, et al., "Increased plasma and pulmonary lymph levels of endothelin during endotoxin shock," Eur. J. of Pharm., 167:427–428 (1989).

Nakajima, et al., "Endothelin–binding inhibitors, BE–18257A and BE–18257B II. Structure determination," J. Antibiotics, 44(12):1348–1356 (1991).

Nakajima, et al., "Structure–activity relationship of endothelin: Importance of charged groups," Biochem. and Biophys. Res. Comm., 163(1):424–429 (1989).

Nirei, et al., "An endothelin $ET_A$ receptor antagonist, FR 139317, ameliorates cerebral vasospasm in dogs," Life Sciences, 52(23):1869–1874 (1993).

Nishikibe, et al., "Antihypertensive effect of a newly synthesized endothelin antagonist, BQ–123, in a genetic hypertensive model," Life Sciences, 52(8):717–724 (1993).

Nogrady, "Pro–drugs and soft drugs," Medicinal Chemistry: A biochemical Approach, Oxford Univ. Press, N.Y., pp. 388–394 (1985).

Ohashi, et al., "Asterric acid, a new endothelin binding inhibitor," J. Antibiotics, 45(10):1684–1685 (1992).

Ösapay and Taylor, "Multicyclic polypeptide model compounds, 1. Synthesis of a tricyclic amphiphilic α–helical peptide using an oxime resin, segment–condensation approach," Amer. Chem. Soc., 112(16):6046–6051 (1990).

Ösapay, et al., "Synthesis of tyrocidine A: Use of oxime resin for peptide chain assembly and cyclization," Tetrahedron Letters, 31(43):6121–6124 (1990).

Palmer, et al., "Nitric oxide release accounts for the biological activity of endothelin–derived relaxing factor," Nature, 327:524–526 (1987).

Ramnarayan, et al., "The effect of polarization energy on the free energy perturbation calculations," J. Chem. Phys., 92(12):7057–7067 (1990).

Saito, et al., "Application of monoclonal antibodies for endothelin to hypertensive research," Hypertension, 15(6)(2):734–738 (1990).

Sakurai, et al., "Cloning of a cDNA encoding a non–isopeptide–selective subtype of the endothelin receptor," Nature, 348:732–735 (1990).

Stein, et al., "The discovery of sulfonamide endothelin antagonists and the development of the orally active $ET_A$ antagonist 5–(dimethylamino)–N–(3, 4–dimethyl–5–isoxazolyl)–1–naphthalenesulfonamide," J. Med. Chem., 37(3):329–331 (1994).

Stewart, et al., "Analytical techniques", Solid Phase Peptide Synthesis, Freeman, W.H. (Ed.), Pierce New York, pp. 105–122 (1984).

Takayanagi, et al., "Multiple subtypes of endothelin receptors in porcine tissues: Characterization by ligand binding, affinity labeling and regional distribution," Regulatory Peptides, 32:23–37 (1991).

Tomita, et al., "Plasma endothelin levels in patients with acute renal failure," N. Eng. J. Medicine, 321(16):1127 (1989).

Yanagisawa and Masaki, "Endothelin, a novel endothelin–derived peptide," Biochem. Pharm., 38(12):1877–1883 1989).

Aumelas, et al., "Determination of the structure of [$Nle^7$]–endothelin by $^1H$ NMR," Int. J. Peptide Protein Res., 37:315–324 (1991).

Blount, et al., "The dependence of the conformations of synthetic polypeptides on amino acid composition," J. Am. Chem. Soc. 82:3787–3789 (1960).

Kotelchuck & Scheraga, "The influence of short–range interactions on protein conformation, II. A model for predicting the α–helical regions of proteins," P.N.A.S. 62:14–21 (1969).

Pabo, et al., "Computer–Aided Model–Building Strategies for Protein Design," Biochemistry 25:5987–5991 (1986).

Perkins, et al., "Proposed solution structure of endothelin," Int. J. Peptide Protein Res., 36:128–133 (1990).

R.S., "Computerized Drug Design: Still Promising, Not Yet Here," *Science* 256:441 (1992).

Saudek, et al., "¹H–NMR study of endothelin, sequence-specific assignment of the spectrum and a solution structure," *FEBS Letters*, 257(1):145–148 (1989).

Saudek, et al., "Solution conformation of endothelin–1 by 1H NMR, CD, and molecular modeling," *Int. J. Peptide Protein Res.*, 37:174–179 (1991).

*Chemistry and Biochemistry of Amino Acids, Peptides and Proteins*, Weinstein, Boris, Editor, Marcel Dekker, Inc. New York and Basel, Chapter 5, pp. 227–357 (1983).

Allen, F.H., *Acta Crystallography*,B35:2231–2239 (1979).

Balasubramanian, R., "New type of representation for mapping chain folding in protein molecules," *Nature* 266:856–857 (1974).

Brint, et al., *J. Computer–Aided Molecular Design* 3:253 (1989).

Cooper, et al., *J. Computer–Aided Molecular Design* 2:311 (1988).

Karplus, M., "Molecular Dynamics:Applications to Proteins in Computer Simulation of Chemical and Biochemical Systems," *Annals N.Y. Acad. Sci.* 482:255–266 (1986).

Kemp, D.S., "Peptidomimetics and the Template Approach to Nucleatio of β–sheets and α–helices in peptides," *Tibech* 8:249–255 (1990).

Ramachandran, et al., "Conformation of Polypeptides," *Adv. Prot. Chem.* 23:283–437 (1968).

Szelke, et al., *In Peptides: Structure & Funciton*, Proceedings of 8thAmer. Peptide Symp., Hruby & Rich, Eds., Pierce Chemical Co., Rockford, Ill., pp. 579–582 (1983).

Weiner, et al., *J. Comput. Chem.* 7:230–252 (1986).

Doherty, "Endothelin: A new challenge," *J. Medicinal Chem.*, 35(9):1493–1508 (1992).

Bolger, et al., Characterization of binding of the $Ca^{++}$ channel antagonist [$^3$H] nitrendipine, to guinea–pig ileal smooth muscle, *J. of Pharmacology and Experimental Therapeutics*, 225:291–309 (1983).

Williams, et al. "Sarafotoxin S6C: An agonist which distinguishes between endothelin receptor subtypes," *Biochem. and Biophys. Research Commun.*, 175(2):556–561 (1991).

Ihara, et al., "An endothelin receptor ($ET_A$) antagonist isolated from *Streptomyces misakiensis*," *Biochem. and Biophys. Research Commun.*, 178(1):132–137 (1991).

Spinella, et al. "Design and synthesis of a specific endothelin 1 antagonist: Effects on pulmonary vasoconstriction," *Proc. Natl. Acad. Sci. USA*, 88p:7443–7446 (1991).

Saeki, et al. "[$Ala^{1,3,11,15}$] endothelin–1 analogs with $ET_B$ agonistic activity," *Biochem. and Biophys. Research Commun.*, 179(1):286–292 (1991).

Gu, et al. "The inhibitory effect of [$D-Arg^1$, D–Phe, $D-Try^{7,9}$, $Leu^{11}$] substance P on endothelin–1 binding sites in rat cardiac membranes," *Biochem. and Biophys. Research Commun.*, 179(1):130–133 (1991).

Panek, et al. "Endothelin and structurally related analogs distinguish between endothelin receptor subtypes," *Biochem. and Biophys. Research Commun.*, 183(2):566–571 (1992).

Ihara, et al. "Biological profiles of highly potent novel endothelin antagonists selective for the $ET_A$ receptor," *Life Sciences*, 50:247–255 (1991).

Hirata, et al., "Receptor binding activity and cytosolic free calcium response by synthetic endothelin analogs in culture rat vascular smooth muscle cells", *Biochem. and Biophys. Research Commun.*, 160:228–234 (1989).

Nakijima, et al., "Synthesis of endothelin–1 analogues, endothelin–3, and sarafotoxin S6b: Structure–activity relationships", *J. of Cardiovascular Pharm.*, 13 (Suppl. 5):S8–S12 (1989).

Yanagisawa, et al., "A novel potent vasoconstrictor peptide produced by vascular entothelial cells," *Nature*, 332:411–415 (1988).

Kashiwabara, et al., "Putative precursors of endothelin have less vasoconstrictor activity in vitro but a potent pressor effect in vivo," *FEBS Letters*, 247(1):73–76 (1989).

von Geldern, et al., "A flurogenic assay for endothelin–converting enzyme" *Peptide Research*, 4(1):32–35 (1991).

Inoue, et al., "The human endothelin family: Three structurally and pharmacologically distinct isopeptides predicted by three separate genes," *Proc. Natl. Acad. Sci. USA*, 86:2863–2867 (1989).

Saida, et al. "A novel peptide, vasoactive intestinal contractor, of a new (endothelin) peptide family," *J. Biol. Chem.*, 264(25):14613–14616 (1989).

Brooks, et al., "Effect of nifedipine on cyclosporine A–induced nephrotoxicity, urinary endothelin excretion and renal endothelin receptor number," *Eur. J. of Pharmacology*, 194:115–117 (1991).

Bolger, et al., "Vascular reactivity, tissue levels, and binding sites for endothelin" A comparison in the spontaneously hypertensive and Wistar–Kyoto rats, *Can. J. Physiol. Pharm.*, 69:406–413 (1990).

Simonson, et al., "Endothelin–1 stimulates contraction of rat glomerular mesangial cells and potentiaties β–Adrenergic–mediated cyclic adenosine monophosphate accumulation," *J. Clin. Invest.*, 85:790–797 (1990).

Stewart, et al., "Increased plasma endothelin–1 in pulmonary hypertension: Marker or mediator of disease?" *Annals of Internal Medicine*, 114(6):464–469 (1991).

Takayanagi, et al., "Presence of non–selective type of endothelin receptor on vascular endothelium and its linkage to vasodilation," *FEBS Letters*, 282(1):103–106 (1991).

Nishikori, et al., "Receptor binding affinity and biological activity of C–terminal elongated forms of endothelin–1", *Neurochem. Int.*, 18(4):535–539 (1991).

Castiglione, et al., "Alanine scan of endothelin," Peptides: Chemistry and Biology, Proc. Amer. Rept. Symp. (Twelfth), J.A. Smith and J.E. Rivier, Eds., ESCOM, Leiden, 1992, pp. 402–403.

Galatino, et al., "D–Amino acid scan of endothelin," Peptides: Chemistry and Biology, Proc. Amer. Rept. Symp. (Twelfth), J.A. Smith and J.E. Rivier, Eds., ESCOM, Leiden, 1992, pp. 404–405.

Filep, et al., "Endothelin–1 induces prostacyclin release from vobine aortic endothelial cells," *Biochem. and Biophys. Research Comm.*, 177(1):171–176 (1991).

Spokes, et al., "Studies with endothelin–3 and endothelin–1 on rat blood pressure and isolated tissues: Evidence for multiple endothelin receptor subtypes," *J. of Cardiovascular Pharmacology*, 13(Suppl. 5):S191–S192 (1989).

Cardell, et al., "Two functional endothelin receptors in guinea–pig pulmonary arteries", *Neurochem. Int.*, 18(4):571–574 (1991).

Borges, et al., "Tissue Selectivity of endothelin," *Eur. J. of Pharmacology*, 165:223–230 (1989).

Ogawa, et al., "Molecular cloning of a non–isopeptide–selective human endothelin receptor," *Biochem. and Biophys. Research Comm.*, 178(1):248–255 (1991).

Schvartz, et al., "Bovine cerebellum endothelin receptor: Solubilization and identification," *Endocrinology*, 126(6):3218–3222 (1990).

Spinella, et al., "A proposed structural model of endothelin," *Peptide Research*, 2(4):286–291 (1989).

Szelke, et al., "Novel transition–state analogue inhibitors of renin," *In Peptides: Structure and Function, Proceedings of the Eighth American peptide symposium*, (Hruby and Rich, Eds.); pp. 579–582, Pierce Chemical Co., Rockford, Illinois (1983).

Allen, et al., "The Cambridge crystallographic data centre: Computer–based search, retrieval, analysis and display of Information," *Acta Crystallogr.*, B35:2331–2339 (1979).

Weiner, et al., "A new force field for molecular mechanical simulation of nucleic acids and proteins," *J. Am. Chem. Soc.*, 106(3):765–784 (Eng.) (1984).

Cooper, et al., "A novel approach to molecular similarity," *J. Comput.–Aided Mol. Design*, 3:253–259 (1989).

Brint, et al., "Upperbound procedures for the identification of similar three–dimensional chemical structures," *J. Comput.–Aided Mol. Design*, 2:311–310 (1988).

Weiner, et al, "An all atom force field for simulations of proteins and nucleic acids," *J. Comput. Chem.*, 7(2):230–252 (1986).

Karplus, M., "Molecular Dynamics: Applications to Proteins," in Computer Simulation of Chemical and Biomolecular Systems, (Bevendge and Jorfensen, Eds.) *Annals of the New York Acad. Science*, 482:255–266 (1986).

Balasubramanian, R., "New type of representation for mapping chain folding in protein molecules," *Nature*, 266:856–857 (1977).

Kemp, D.S., "Peptidomimetrics and the template approach to nucleation of β–sheets and α–helices in peptides," *Tibtech*, 8:249–255 (1990).

Shimazaki, et al., "Piperazine derivatives", *Chem. Abs.* 106:558 (abs.#331(4a) (1987).

| ATOM | | AMINO ACID | | x | y | z |
|---|---|---|---|---|---|---|
| 168 | N | TYR | 13 | -1.328 | -1.642 | 2.219 |
| 169 | CA | TYR | 13 | -0.372 | -0.772 | 1.501 |
| 170 | C | TYR | 13 | 0.256 | 0.413 | 2.333 |
| 171 | O | TYR | 13 | 0.467 | 1.512 | 1.814 |
| 172 | CB | TYR | 13 | -1.166 | -0.275 | 0.244 |
| 173 | CG | TYR | 13 | -0.891 | -1.002 | -1.079 |
| 174 | CD1 | TYR | 13 | 0.206 | -0.616 | -1.861 |
| 175 | CD2 | TYR | 13 | -1.803 | -1.929 | -1.578 |
| 176 | CE1 | TYR | 13 | 0.357 | -1.132 | -3.151 |
| 177 | CE2 | TYR | 13 | -1.648 | -2.446 | -2.867 |
| 178 | CZ | TYR | 13 | -0.575 | -2.030 | -3.652 |
| 179 | OH | TYR | 13 | -0.477 | -2.474 | -4.945 |
| 180 | H | TYR | 13 | -2.339 | -1.506 | 2.125 |
| 181 | HA | TYR | 13 | 0.480 | -1.403 | 1.173 |
| 182 | 1HB | TYR | 13 | -0.959 | 0.794 | 0.058 |
| 183 | 2HB | TYR | 13 | -2.261 | -0.234 | 0.424 |
| 184 | HD1 | TYR | 13 | 0.914 | 0.107 | -1.490 |
| 185 | HD2 | TYR | 13 | -2.661 | -2.228 | -0.991 |
| 186 | HE1 | TYR | 13 | 1.190 | -0.809 | -3.758 |
| 187 | HE2 | TYR | 13 | -2.371 | -3.136 | -3.267 |
| 188 | HH | TYR | 13 | 0.147 | -1.918 | -5.413 |
| 189 | N | PHE | 14 | 0.747 | 0.163 | 3.561 |
| 190 | CA | PHE | 14 | 2.153 | 0.507 | 3.851 |
| 191 | C | PHE | 14 | 3.113 | -0.580 | 3.317 |
| 192 | O | PHE | 14 | 2.823 | -1.596 | 2.678 |
| 193 | CB | PHE | 14 | 2.441 | 0.997 | 5.320 |
| 194 | CG | PHE | 14 | 2.917 | 2.465 | 5.342 |
| 195 | CD1 | PHE | 14 | 4.249 | 2.835 | 5.646 |

FIG. 1A

| ATOM | | AMINO ACID | | x | y | z |
|---|---|---|---|---|---|---|
| 196 | CD2 | PHE | 14 | 2.030 | 3.441 | 4.914 |
| 197 | CE1 | PHE | 14 | 4.632 | 4.171 | 5.530 |
| 198 | CE2 | PHE | 14 | 2.413 | 4.769 | 4.799 |
| 199 | CZ | PHE | 14 | 3.732 | 5.133 | 5.108 |
| 200 | H | PHE | 14 | 0.446 | -0.784 | 3.843 |
| 201 | HA | PHE | 14 | 2.412 | 1.352 | 3.190 |
| 202 | 1HB | PHE | 14 | 3.212 | 0.357 | 5.796 |
| 203 | 2HB | PHE | 14 | 1.564 | 0.861 | 5.977 |
| 204 | HD1 | PHE | 14 | 4.975 | 2.097 | 5.938 |
| 205 | HD2 | PHE | 14 | 1.036 | 3.144 | 4.576 |
| 206 | HE1 | PHE | 14 | 5.655 | 4.464 | 5.769 |
| 207 | HE2 | PHE | 14 | 1.718 | 5.489 | 4.414 |
| 208 | HZ | PHE | 14 | 4.031 | 6.163 | 5.002 |
| 209 | N | CYS | 15 | 4.363 | -0.256 | 3.453 |
| 210 | CA | CYS | 15 | 5.054 | 0.312 | 2.306 |
| 211 | C | CYS | 15 | 5.995 | -0.978 | 1.887 |
| 212 | O | CYS | 15 | 7.124 | -0.971 | 2.368 |
| 213 | CB | CYS | 15 | 4.691 | 1.853 | 1.772 |
| 214 | SG | CYS | 15 | 3.045 | 2.674 | 1.176 |
| 215 | H | CYS | 15 | 4.827 | -1.080 | 3.855 |
| 216 | HA | CYS | 15 | 5.873 | 0.775 | 2.891 |
| 217 | 1HB | CYS | 15 | 5.375 | 2.071 | 0.937 |
| 218 | 2HB | CYS | 15 | 4.993 | 2.567 | 2.566 |
| 219 | N | HIS | 16 | 5.671 | -2.215 | 1.321 |
| 220 | CA | HIS | 16 | 6.729 | -3.337 | 1.051 |
| 221 | C | HIS | 16 | 7.968 | -2.786 | 0.234 |
| 222 | O | HIS | 16 | 9.135 | -2.937 | 0.599 |
| 223 | CB | HIS | 16 | 6.241 | -4.628 | 0.253 |

FIG. 1B

| ATOM | | AMINO ACID | | x | y | z |
|---|---|---|---|---|---|---|
| 224 | CG | HIS | 16 | 6.034 | -6.084 | 0.753 |
| 225 | ND1 | HIS | 16 | 5.158 | -6.869 | 0.000 |
| 226 | CD2 | HIS | 16 | 6.909 | -6.954 | 1.473 |
| 227 | CE1 | HIS | 16 | 5.558 | -8.131 | 0.346 |
| 228 | NE2 | HIS | 16 | 6.572 | -8.293 | 1.243 |
| 229 | H | HIS | 16 | 4.669 | -2.435 | 1.407 |
| 230 | HA | HIS | 16 | 7.153 | -3.673 | 2.021 |
| 231 | 1HB | HIS | 16 | 6.962 | -4.851 | -0.562 |
| 232 | 2HB | HIS | 16 | 5.348 | -4.333 | -0.322 |
| 233 | HD2 | HIS | 16 | 7.804 | -6.659 | 2.004 |
| 234 | HE1 | HIS | 16 | 5.122 | -8.988 | -0.160 |
| 235 | HE2 | HIS | 16 | 7.002 | -9.176 | 1.548 |
| 236 | N | LEU | 17 | 7.643 | -2.129 | -0.884 |
| 237 | CA | LEU | 17 | 8.164 | -0.791 | -1.284 |
| 238 | C | LEU | 17 | 9.234 | -0.020 | -0.403 |
| 239 | O | LEU | 17 | 10.235 | 0.412 | -0.958 |
| 240 | CB | LEU | 17 | 6.866 | 0.045 | -1.588 |
| 241 | CG | LEU | 17 | 5.860 | -0.478 | -2.668 |
| 242 | CD1 | LEU | 17 | 4.502 | 0.238 | -2.582 |
| 243 | CD2 | LEU | 17 | 6.419 | -0.342 | -4.091 |
| 244 | H | LEU | 17 | 6.634 | -2.257 | -1.012 |
| 245 | HA | LEU | 17 | 8.677 | -0.949 | -2.251 |
| 246 | 1HB | LEU | 17 | 7.159 | 1.076 | -1.860 |
| 247 | 2HB | LEU | 17 | 6.315 | 0.177 | -0.638 |
| 248 | HG | LEU | 17 | 5.647 | -1.553 | -2.497 |
| 249 | 1HD1 | LEU | 17 | 4.588 | 1.330 | -2.732 |
| 250 | 2HD1 | LEU | 17 | 3.792 | -0.139 | -3.345 |
| 251 | 3HD1 | LEU | 17 | 4.011 | 0.075 | -1.604 |

FIG. 1C

| ATOM | | AMINO ACID | | x | y | z |
|---|---|---|---|---|---|---|
| 252 | 1HD2 | LEU | 17 | 7.352 | -0.920 | -4.222 |
| 253 | 2HD2 | LEU | 17 | 5.710 | -0.723 | -4.850 |
| 254 | 3HD2 | LEU | 17 | 6.643 | 0.709 | -4.352 |
| 255 | N | ASP | 18 | 9.052 | 0.140 | 0.921 |
| 256 | CA | ASP | 18 | 10.073 | 0.640 | 1.895 |
| 257 | C | ASP | 18 | 11.354 | -0.244 | 2.128 |
| 258 | O | ASP | 18 | 12.432 | 0.339 | 2.249 |
| 259 | CB | ASP | 18 | 9.314 | 0.902 | 3.234 |
| 260 | CG | ASP | 18 | 10.068 | 1.683 | 4.303 |
| 261 | OD1 | ASP | 18 | 10.501 | 1.186 | 5.336 |
| 262 | OD2 | ASP | 18 | 10.184 | 3.002 | 3.999 |
| 263 | H | ASP | 18 | 8.240 | -0.385 | 1.281 |
| 264 | HA | ASP | 18 | 10.438 | 1.616 | 1.516 |
| 265 | 1HB | ASP | 18 | 9.019 | -0.060 | 3.694 |
| 266 | 2HB | ASP | 18 | 8.365 | 1.439 | 3.058 |
| 267 | HD2 | ASP | 18 | 10.711 | 3.405 | 4.689 |
| 268 | N | ILE | 19 | 11.291 | -1.597 | 2.214 |
| 269 | CA | ILE | 19 | 12.534 | -2.451 | 2.172 |
| 270 | C | ILE | 19 | 13.306 | -2.287 | 0.810 |
| 271 | O | ILE | 19 | 14.495 | -1.962 | 0.824 |
| 272 | CB | ILE | 19 | 12.313 | -3.972 | 2.553 |
| 273 | CG1 | ILE | 19 | 11.698 | -4.207 | 3.966 |
| 274 | CG2 | ILE | 19 | 13.644 | -4.786 | 2.469 |
| 275 | CD1 | ILE | 19 | 11.149 | -5.631 | 4.211 |
| 276 | H | ILE | 19 | 10.353 | -1.985 | 2.057 |
| 277 | HA | ILE | 19 | 13.225 | -2.050 | 2.941 |
| 278 | HB | ILE | 19 | 11.609 | -4.394 | 1.807 |
| 279 | 1HG1 | ILE | 19 | 10.869 | -3.496 | 4.136 |

FIG. 1D

| ATOM | | AMINO ACID | | x | y | z |
|---|---|---|---|---|---|---|
| 280 | 2HG1 | ILE | 19 | 12.443 | -3.956 | 4.748 |
| 281 | 1HG2 | ILE | 19 | 14.427 | -4.360 | 3.125 |
| 282 | 2HG2 | ILE | 19 | 13.533 | -5.849 | 2.745 |
| 283 | 3HG2 | ILE | 19 | 14.064 | -4.794 | 1.445 |
| 284 | 1HD1 | ILE | 19 | 11.938 | -6.404 | 4.158 |
| 285 | 2HD1 | ILE | 19 | 10.695 | -5.723 | 5.215 |
| 286 | 3HD1 | ILE | 19 | 10.374 | -5.908 | 3.473 |
| 287 | N | ILE | 20 | 12.664 | -2.553 | -0.343 |
| 288 | CA | ILE | 20 | 13.365 | -2.545 | -1.666 |
| 289 | C | ILE | 20 | 13.685 | -1.096 | -2.220 |
| 290 | O | ILE | 20 | 14.791 | -0.920 | -2.737 |
| 291 | CB | ILE | 20 | 12.692 | -3.617 | -2.615 |
| 292 | CG1 | ILE | 20 | 12.946 | -5.084 | -2.131 |
| 293 | CG2 | ILE | 20 | 13.168 | -3.527 | -4.086 |
| 294 | CD1 | ILE | 20 | 11.962 | -6.144 | -2.665 |
| 295 | H | ILE | 20 | 11.677 | -2.804 | -0.225 |
| 296 | HA | ILE | 20 | 14.385 | -2.949 | -1.497 |
| 297 | HB | ILE | 20 | 11.599 | -3.432 | -2.613 |
| 298 | 1HG1 | ILE | 20 | 12.905 | -5.133 | -1.026 |
| 299 | 2HG1 | ILE | 20 | 13.985 | -5.387 | -2.372 |
| 300 | 1HG2 | ILE | 20 | 14.271 | -3.462 | -4.167 |
| 301 | 2HG2 | ILE | 20 | 12.845 | -4.379 | -4.710 |
| 302 | 3HG2 | ILE | 20 | 12.754 | -2.633 | -4.570 |
| 303 | 1HD1 | ILE | 20 | 11.979 | -6.224 | -3.767 |
| 304 | 2HD1 | ILE | 20 | 12.208 | -7.149 | -2.274 |
| 305 | 3HD1 | ILE | 20 | 10.920 | -5.926 | -2.366 |
| 306 | N | TRP | 21 | 12.811 | -0.066 | -2.118 |
| 307 | CA | TRP | 21 | 13.169 | 1.346 | -2.490 |

FIG. 1E

| ATOM | | AMINO ACID | | x | y | z |
|---|---|---|---|---|---|---|
| 308 | C | TRP | 21 | 12.547 | 2.444 | -1.577 |
| 309 | O | TRP | 21 | 12.235 | 2.259 | -0.399 |
| 310 | CB | TRP | 21 | 12.813 | 1.649 | -3.981 |
| 311 | CG | TRP | 21 | 13.717 | 0.954 | -5.007 |
| 312 | CD1 | TRP | 21 | 13.406 | -0.249 | -5.667 |
| 313 | CD2 | TRP | 21 | 15.041 | 1.214 | -5.313 |
| 314 | NE1 | TRP | 21 | 14.525 | -0.792 | -6.329 |
| 315 | CE2 | TRP | 21 | 15.527 | 0.134 | -6.093 |
| 316 | CE3 | TRP | 21 | 15.905 | 2.276 | -4.937 |
| 317 | CZ2 | TRP | 21 | 16.884 | 0.095 | -6.481 |
| 318 | CZ3 | TRP | 21 | 17.233 | 2.234 | -5.366 |
| 319 | CH2 | TRP | 21 | 17.718 | 1.156 | -6.120 |
| 320 | H | TRP | 21 | 12.016 | -0.258 | -1.492 |
| 321 | HA | TRP | 21 | 14.259 | 1.493 | -2.349 |
| 322 | HC | TRP | 21 | 12.403 | 3.463 | -1.983 |
| 323 | 1HB | TRP | 21 | 11.754 | 1.389 | -4.172 |
| 324 | 2HB | TRP | 21 | 12.877 | 2.734 | -4.187 |
| 325 | HD1 | TRP | 21 | 12.452 | -0.745 | -5.568 |
| 326 | HE1 | TRP | 21 | 14.655 | -1.756 | -6.657 |
| 327 | HE3 | TRP | 21 | 15.545 | 3.101 | -4.340 |
| 328 | HZ2 | TRP | 21 | 17.268 | -0.743 | -7.043 |
| 329 | HZ3 | TRP | 21 | 17.900 | 3.043 | -5.108 |
| 330 | HH2 | TRP | 21 | 18.755 | 1.144 | -6.425 |

FIG. 1F

CYCLIC PEPTIDE SURFACE FEATURE MIMICS OF ENDOTHELIN

This application is a Continuation-in-part of U.S. application Ser. No. 08/223,513, filed Apr. 5, 1994, now abandoned, and also a Continuation-in-part of U.S. application Ser. No. 07/900,623, filed Jun. 18, 1992, now abandoned, which is a Continuation-in-part of U.S. application Ser. No. 07/628,111, filed Dec. 14, 1990, now U.S. Pat. No. 5,331,573.

FIELD OF THE INVENTION

The present invention relates to the design of compounds that mimic surface features of the endothelin family of peptides. In particular, cyclic peptides are provided that modulate that activity of endothelin. More particularly, cyclic peptides that specifically inhibit the activity of endothelin are provided.

BACKGROUND OF THE INVENTION

The vascular endothelium releases a variety of vasoactive substances, including the endothelium-derived vasoconstrictor prptide, endothelin (ET) (see, e.g., Vanhoutte et al. (1986) *Annual Rev. Physiol.* 48: 307-320; Furchgott and Zawadski (1980) *Nature* 288: 373-376). Endothelin, which was originally identified in the culture supernatant of porcine aortic endothelial cells (see, Yanagisawa et al. (1988) *Nature* 332: 411-415), is a potent twenty-one amino acid peptide vasoconstrictor. It is the most potent vasopressor known and is produced by numerous cell types, including the cells of the endothelium, trachea, kidney and brain. Endothelin is synthesized as a two hundred and three amino acid precursor preproendothelin that contains a signal sequence which is cleaved by an endogenous protease to produce a thirty-eight (human) or thirty-nine (porcine) amino acid peptide. This intermediate, referred to as big endothelin, is processed in vivo to the mature biologically active form by a putative endothelin-converting enzyme (ECE) that appears to be a metal-dependent neutral protease (see, e.g., Kashiwabara et al. (1989) *FEBS Lttrs.* 247: 337-340). Cleavage is required for induction of physiological responses (see, e.g., von Geldern et al. (1991) *Peptide Res.* 4: 32-35). In porcine aortic endothelial cells, the thirty-nine amino acid intermediate, big endothelin, is hydrolyzed at the $Trp^{21}$-$Val^{22}$ bond to generate endothelin-1 and a C-terminal fragment. A similar cleavage occurs in human cells from a thirty-eight amino acid intermediate.

Three distinct endothelin isopeptides, endothelin-1, endothelin-2 and endothelin-3, that exhibit potent vasoconstrictor activity have been identified. The family of three isopeptides endothelin-1, endothelin-2 and endothelin-3 are encoded by a family of three genes (see, Inoue et al. (1989) *Proc. Natl. Acad. Sci. USA* 86: 2863-2867; see, also Thea et al. (1989) *J. Biol. Chem.* 264: 14613-14616). The nucleotide sequences of the three human genes are highly conserved within the region encoding the mature 21 amino acid peptides and the C-terminal portions of the peptides are identical. Endothelin-2 is ($Trp^6$, $Leu^7$) endothelin-1 and endothelin-3 is ($Thr^2$, $Phe^4$, $Thr^5$, $Tyr^6$, $Lys^7$, $Tyr^{14}$) endothelin-1. These peptides are, thus, highly conserved at the C-terminal ends.

Release of endothelin from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194:115-117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

The endothelins (referred to collectively as endothelin) or one or more endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69: 406–413). In isolated vascular strips, for example, endothelin-1 is a potent ($EC_{50}=4\times10^{-10}M$), slow acting, but persistent, contractile agent. In vivo, a single dose elevates blood pressure in about twenty to thirty minutes. Endothelin-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160:179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797).

There are specific high affinity binding sites (dissociation constants in the range of $2$–$6\times10^{-10}M$) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake *Atractaspis eingadensis* that cause severe coronary vasospasm in snake bite victims, have structural and functional homology to endothelin-1 and bind competitively to the same cardiac membrane receptors (Kloog et al. (1989) *Trends Pharmacol. Sci.* 10:21 2–214).

Two distinct endothelin receptors, designated $ET_A$ and $ET_B$, have been identified and there is evidence that other subtypes exist (see, e.g., Emori et al. (1990) *FEBS Lett.* 263:261–264; and Sokolovsky et al. (1992) *J. Biol. Chem.* 267:20551–20554). DNA clones encoding the $ET_A$ and $ET_B$ receptors have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain.

The distribution of receptor subtypes is tissue specific (Martin et al. (1989) *Biochem. Biophys. Res. Commun.* 162: 130–137) and the affinity of each receptor for members of the endothelin family of peptides can be distinguished. $ET_A$ receptors appear to be selective for endothelin-1 and are predominant in cardiovascular tissues. $ET_B$ receptors are predominant in non-cardiovascular tissues, including the central nervous system and kidney, and interact with the three endothelin isopeptides (Sakurai et al. (1990) *Nature* 348: 732–734). In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation (Takayanagi et al. (1991) *FEBS Lett.* 282: 103–106) and have been associated with bronchoconstrictive disorders. The $ET_A$ receptor appears to mediate the principal part of the vasoconstriction induced by ET-1 (Ihara et al. (1993) *Lif. Sci* 50:247–255) and the $ET_B$ subtype mediates endothelium-dependent vasodilation (Takayanagi et al. (1991) *FEBS Lett.* 282:103–106). Selective agonist-induced stimulation of $ET_B$, however, can induce vasoconstriction (see, e.g., MCMurdo et al. (1993) *Br. J. Pharmac.* 108:557–561; and Moreland et al. (1992) *Biochem. Biophys. Res. Commun.* 184:100–106).

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Endothelin plasma levels are elevated in certain disease states. Endothelin-1 plasma levels in healthy individuals, as measured by radio-immunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels as high as 35 pg/ml have been observed (see, Stewart et al. (1991) *Annals Internal Med.* 114: 464–469). Because endothelin is likely to be a local, rather than a systemic, regulating factor, it is probable that the levels of endothelin at the endothelium/smooth muscle interface are much higher than circulating levels.

Endothelin Agonists and Antagonists

Because endothelin is associated with certain disease states and is implicated in numerous physiological effects, compounds that can interfere with or potentiate endothelin-associated activities, such as endothelin-receptor interaction and vasoconstrictor activity, are of interest. A number of compounds that exhibit endothelin antagonistic activity have been identified. These include cyclic pentapeptides, acyltripeptides, hexapeptide analogs, certain anthraquinone, derivatives, indanecarboxylic acids, certain N-pyriminylbenzenesulfonamides, certain benzenesulfonamides, and certain naphthalenesulfonamides (Nakajima et al. (1991) *J. Antibiot.* 44:1348–1356; Miyata et al. (1992) *J. Antibiot.* 45:74–8; Ishikawa et al. (1992) *J. Med. Chem.* 35:2139–2142; U.S. Pat. No. 5,114,918 to Ishikawa et al.; EP A1 0 569 193; EP A10 558 258; EP A10 436 189 to BANYU PHARMACEUTICAL CO., LTD (Oct. 7, 1991); Canadian Patent Application 2,067,288; Canadian Patent Application 2,071,193; U.S. Pat. No. 5,208,243; U.S. Pat. No. 5,270,313; Cody et al. (1993) *Med. Chem. Res.* 3:154–162; Miyata et al. (1992) *J. Antibiot* 45:1041–1046; Miyata et al. (1992) *J. Antibiot* 4–5:1029–1040, Fujimoto et al. (1992) *FEBS Lett.* 305:41–44; Oshashi et al. (1002) *J. Antibiot* 45:1684–1685; EP A1 0 496 452; Clozel et al. (1993) *Nature* 365:759–761; International Patent Application WO93/08799; Nishikibe et al. (1993) *Life Sci.* 52:717–724; and Benigni et al. (1993) *Kidney Int.* 44:440–444).

In particular, a fermentation product of *Streptomyces misakiensis*, designated BE-18257B, has been identified as an $ET_A$ receptor antagonist. BE-18257B is a cyclic pentapeptide, cyclo(D-Glu-L-Ala-allo-D-Ile-L-Leu-D-Trp), which inhibits $^{125}$I-labelled endothelin-1 binding in cardiovascular tissues in a concentration-dependent manner ($IC_{50}$ 1.4 µM in aortic smooth muscle, 0.8/µM in ventricle membranes and 0.5 µM in cultured aortic smooth muscle cells), but fails to inhibit binding to receptors in tissues in which $ET_B$ receptors predominate at concentrations up to 100 µM. Cyclic pentapeptides related to BE-18257B, such as cyclo(D-Asp-Pro-D-Val-Leu-D-Trp) (BQ-123), have been synthesized and shown to exhibit activity as $ET_A$ receptor antagonists (see, U.S. Pat. No. 5,114,918 to Ishikawa et al.; see, also, EP A1 0 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to $ET_A$ receptors.

Numerous other peptide and non-peptidic $ET_A$ antagonists have been identified (see, e.g., U.S. Pat. Nos. 5,352,800, 5,334,598, 5,352,659, 5,248,807, 5,240,910, 5,198,548, 5,187,195, 5,082,838).

Endothelin Antagonists and Agonists as Therapeutic Agents

In view of the numerous physiological effects of endothelin and its association with certain diseases, endothelin is believed to play a critical role in pathophysiological conditions, including hypertension, artherosclerois, other vascular disorders, gastrointestinal disorders, renal failure, asthma, pulmonary hypertension, endotoxin shock, coronary vasospasm, cerebral vasospasm and others (see, e.g., Saito et al. (1990) *Hypertension* 15: 734–738; Tomita et al. (1989) *N. Engl. J. Med.* 321: 1127; Kurihara et al. (1989) *J. Cardiovasc. Pharmacol.* 13(Suppl. 5): S13–S17; Doherty (1992) *J. Med. Chem.* 35: 1493–1508; Morel et al. (1989) *Eur. J. Pharmacol.* 167: 427–428). More detailed knowledge of the function and structure of the endothelin peptide family should provide insight in the progression and treatment of such conditions.

It has been recognized that compounds that exhibit activity in standard in vitro assays to assess endothelin antagonist activity at $IC_{50}$ or $EC_{50}$ concentrations on the order of $10^{-4}$ or lower have pharmacological utility (see, e.g., U.S. Pat. Nos. 5,352,800, 5,334,598, 5,352,659, 5,248,807, 5,240,910, 5,198,548, 5,187,195, 5,082,838). Such compounds are disclosed as being useful for the treatment of hypertension such as peripheral circulatory failure, heart disease such as angina pectoris, cardiomyopathy, arteriosclerosis, myocardial infarction, pulmonary hypertension, vasospasm, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly post-ischemic renal failure, cyclosporine nephrotoxicity, such as acute renal failure, colitis, as well as other inflammatory diseases, endotoxic shock caused by or associated with endothelin.

To aid in gaining further understanding of and to develop treatments for endothelin-mediated or related disorders, there is a need to identify compounds that modulate or alter endothelin activity. Identification of compounds that modulate endothelin activity, such as compounds that act as specific antagonists or agonists, may not only aid in elucidating the function of endothelin, but may yield in therapeutically useful compounds. In particular, compounds that specifically interfere with the interaction of endothelin peptides with $ET_A$, $ET_B$ or other receptors should be useful in identifying essential characteristics of endothelin peptides, should aid in the design of therapeutic agents, and may be useful as disease specific therapeutic agents.

The studies and methods discussed above regarding the selection and design of compounds that provide insights into the structure and function of endothelin and into the structure of compounds that modulate the activity the endothelin peptides provide an imprecise non-systematic approach to identification of endothelin antagonists and agonists. The methods of rational drug design that have been described in copending U.S. application Ser. No. 08/223,514 and U.S. Pat. No. 5,331,573, provide a means to design compounds that mimic surface features of target peptides and that thereby may have the ability to specifically modulate the biological activity of the target peptide. Application of these methods to design compounds that modulate endothelin activity may provide therapeutically useful compounds.

Therefore, it is an object herein to provide compounds that mimic surface features of the endothelin peptides. It is also an object to provide compounds that mimic the surface features of endothelin peptides and that thereby have the ability to modulate the biological activity of one or more of the endothelin isopeptides. It is another object herein, to provide compounds that have activity as specific endothelin antagonists. It is also an object herein to provide compounds that specifically interact with or inhibit the interaction of endothelin peptides with $ET_A$ or $ET_B$ receptors. It is also an object herein to provide methods for distinguishing between $ET_A$ and $ET_B$ receptors and methods for identifying and purifying endothelin-specific receptors.

SUMMARY OF THE INVENTION

Cyclic peptides that mimic surface features of the endothelin peptides are provided. The cyclic peptides provided herein are pentapeptides, hexapeptides and heptapeptides that contain an L-Trp, D-Trp residue or a derivative of D- or L-Trp, such as N-Me-Trp. Pharmaceutically acceptable salts, esters and other derivatives of the peptides are also provided.

The cyclic peptides provided herein modulate the activity of one or more members of the endothelin family of peptides. In particular, cyclic peptides that inhibit or interfere with the interaction of endothelin with endothelin-specific receptors or with endothelin-mediated biological responses and thereby act as specific endothelin antagonists are provided.

The cyclic peptides were designed by using the ab initio methods described in copending U.S. application Ser. No. 08/223,513 and U.S. Pat. No. 5,331,573 to simulate and determine the most probable conformations of endothelin-1 based on its primary amino acid sequence. The portions of endothelin-1 responsible for receptor interaction and biological activity were also identified. This information regarding the most probable conformation of endothelin and portions of endothelin-1 responsible for receptor interaction and biological activity was used to design cyclic peptides, containing from five to seven amino acid residues. In particular, the cyclic peptides were designed by comparing the structures of cyclic peptides containing between five and seven D-Ala and L-Ala residues with the coordinates of the most probable conformation of the terminal region of endothelin-1 and selecting the cyclic peptides that best match surface features of the C-terminal residues of endothelin. The coordinates of residues 13–21 of the most probable conformation of endothelin are set forth in FIG. 1. Coordinates of Ala-containing cyclic peptides were compared with the coordinates of the cyclic peptides with the coordinates of the C-terminal portion of endothelin-1, and the cyclic peptides that best match the coordinates of the C-terminal residues of endothelin were selected. A best match is defined as a goodness of fit of between about 60% and about 100%. Goodness of fit is defined by Equation (1):

$$G=100(1-X/n), \qquad (1)$$

where $$X = \sum_{i=1}^{n} ((r(a)-r(b)) \times (r(a)-r(b)))_i$$

for i=1–n in which r(a) and r(b) are the coordinates of ith atom of molecule (a) and (b), respectively, molecule (a) is the C-terminal portion of endothelin-1, molecule (b) is the cyclic peptide, and n is 9. The goodness of fit computation incorporates the positions of the $C^\alpha$ and $C^\beta$ main chain atoms. If two molecules are identical, then G=100%.

The selected D-Ala and L-Ala peptides were then compared with the C-terminal region of endothelin-1 and modified by the replacement of one or more of the Ala residues with other residues that improve the match with the C-terminal region of endothelin. The resulting cyclic peptides mimic certain surface features of endothelin and should have the ability to modulate the activity of endothelin.

Several groups of cyclic peptides have been identified. One group of the cyclic peptides includes peptides that contain a D-Trp residue, or a derivative of D-Trp, such as N-Me-D-Trp, fixed such that its orientation and disposition is the same as the terminal Trp$^{21}$ residue in endothelin-1. Another group of cyclic peptides includes peptides that do not include such a D-Trp residue, but include an L-Trp residue. Selected cyclic peptides in each group have been synthesized and their biological activity as modulators of endothelin-1 activity have been assessed.

Thus cyclic peptides, or pharmaceutically acceptable salts, esters or other derivatives of the peptides, containing between 5 and 7 residues that match the surface features of the C-terminal portion of endothelin-1 are provided. The cyclic peptides have between 5 and 7 residues that are selected such that the peptides have a goodness of fit as defined by Equation (1) of at least about 60%, preferably at least about 80%, with the coordinates, which are set forth in FIG. 1, of the C-terminal region of endothelin; provided that $X^1$, $X^2$, $X^3$, $X^4$ are selected such that:

(i) if the peptide is a cyclic pentapeptide, it has the structure, in which the designations D- and L- refer to the stereochemistry of the amino acid residue and the superscripts refer to the position relative to the specified Trp residue if the molecule is linearized with the Trp residue at the end, D-$X^1$-L-$X^2$-D-$X^3$-L-$X^4$-D-Trp, D-$X^1$-D-$X^2$-L-$X^3$-D-$X^4$-L-Trp, D-$X^1$-L-$X^2$-D-$X^3$-D-$X^4$-D-Trp, D-$X^1$-L-$X^2$-D-$X^3$-L-$X^4$-L-Trp, with D-$X^1$-L-$X^2$-D-$X^3$-L-$X^4$-D-Trp, D-$X^1$-D-$X^2$-L-$X^3$-D-$X^4$-L-Trp or D-$X^1$-L-$X^2$-D-$X^3$-L-$X^4$-L-Trp preferred, or it includes an amino acid or amino acid that is not optically active in place of one or more of $X^1$–$X^4$;

(ii) if the structure is D-$X^1$-L-$X^2$-D-$X^3$-L-$X^4$-D-Trp, then residue $X^2$ is not L-Trp;

(iii) if the peptide is a cyclic heptapeptide or cyclic hexapeptide, it has any of the backbone structures set forth in (ii), but with an additional one or two residues inserted therein; and (iv) the peptide is not cyclo(D-Asp-Ala-D-Ala-Ala-D-Trp) cyclo(D-Asp-Pro-D-Val-Leu-D-Trp); cyclo(D-Glu-L-Ala-allo-D-Ile-L-Leu-D-Trp); cyclo(D-Glu-Ser-D-Val-Leu-D-Trp); cyclo(D-Cys($O_3$Na)-Ala-D-Val-Leu-D-TrP); cyclo(D-Asp-Lys-D-Val-Leu-D-Trp); cyclo(D-Cys($O_3$Na)-Pro-D-Val-Leu-D-Trp); cyclo(D-Cys($O_3$Na)-Pro-D-Val-Nle-D-Trp); cyclo(D-Asp-Leu-D-Val-Leu-D-Trp); cyclo(D-Glu-Ala-D-Val-Leu-D-Trp); cyclo(D-Glu-Ala-D-Alle-Leu-D-Trp); cyclo(D-Glu-Pro-D-Val-Leu-D-Trp); cyclo(D-Asp-Gly-D-Val-Leu-D-Trp); cyclo(D-Asp-Ala-D-Val-Leu-D-Trp); cyclo(D-Asp-Leu-D-Val-Leu-D-Trp); cyclo(D-Asp-MeAla-D-Val-Leu-D-Trp); cyclo(D-Asp-Met-D-Val-Leu-D-Trp); cyclo(D-Asp-Trp-D-Val-Leu-D-Trp); cyclo(D-Asp-His-D-Val-Leu-D-Trp); cyclo(D-Asp-Arg-D-Val-Leu-D-Trp); cyclo(D-Asp-Orn-D-Val-Leu-D-Trp); cyclo(D-Asp-Gln-D-Val-Leu-D-Trp); cyclo(D-Asp-Asp-D-Val-Leu-D-Trp); cyclo(D-Asp-Cys($O_3$Na)-D-Val-Leu-D-Trp); cyclo(D-Asp-Cys-D-Val-Leu-D-Trp); cyclo(D-Asp-Ser-D-Val-Leu-D-Trp); cyclo(D-Asp-Thr-D-Val-Leu-D-Trp); cyclo(D-Asp-Ala-D-Leu-Leu-D-Trp); cyclo(D-Asp-Ala-D-Thr-Leu-D-Trp); cyclo(D-Asp-Pro-D-Ile-Leu-D-Trp); cyclo(D-Asp-Pro-D-Alle-Leu-D-Trp); cyclo(D-Asp-Pro-D-Nle-Leu-D-Trp); cyclo(D-Asp-Pro-D-Phg-Leu-D-Trp); cyclo(D-Asp-Pro-D-Nva-Leu-D-Trp); cyclo(D-Asp-Ser-D-Val-Nlle-D-Trp); cyclo(D-Asp-Ser-D-Val-Met-D-Trp); cyclo(D-Asp-Asp-D-Val-Ala-D-Trp); cyclo(D-Asp-Ala-D-Val-Pro-D-Trp); cyclo(D-Asp-Pro-D-Val-Ile-D-Trp); cyclo(D-Asp-Pro-D-Val-Nlle-D-Trp); cyclo(D-CYs($O_3$Na)-Cys($O_3$Na)-D-Val-Leu-D-Trp); cyclo(D-Cys($O_3$Na)-Pro-D-Alle-Leu-D-Trp); cyclo(D-Asp-Val-D-Val-Leu-D-Trp); cyclo(D-Asp-Pro-D-Val-Nva-D-Trp); cyclo(D-Asp-Nle-D-Val-Leu-D-Trp); cyclo(D-Asp-Pip-D-Val-Leu-D-Trp); cyclo(D-Asp-Phe-D-Val-Leu-D-Trp); cyclo(D-Cys($O_3$Na)-Glu-D-Val-Leu-D-Trp); cyclo(D-Cys($O_3$Na)-Lys-D-Val-Leu-D-Trp); cyclo(D-Asp-Pro-D-Val-Leu-D-Trp(CHO)); cyclo(D-Glu-Ala-D-Alle-Leu-D-Trp(CHO)); cyclo(D-Asp-Pro-D-Alle-Leu-D-Trp(CHO)); cyclo(D-Asp-Ser-D-Val-Nle-D-Trp(CHO)); cyclo(D-Asp-Met-D-Val-Leu-D-Trp(CHO)); cyclo(D-Asp-Pro-D-Val-Nva-D-Trp(CHO)); cyclo(D-Asp-Lys(CHO)-D-Val-Leu-D-Trp(CHO)); cyclo(D-Asp-Met(O)-D-Val-Leu-D-Trp(CHO)); cyclo(D-Asp(ONa)-Pro-D-Val-Leu-D-Trp); cyclo(D-Asp-Pro-D-Pen-Leu-D-Trp); cyclo(D-Asp-Aib-D-Val-Leu-D-Trp); cyclo(D-Asp-Pro-D-Aib-Leu-D-Trp); cyclo(D-Asp-Pro-D-$AC_5C$-Leu-D-Trp); cyclo(D-Asp-Pro-$AC_6C$-Leu-D-Trp); cyclo(D-Asp-Sar-D-Val-Leu-D-Trp); cyclo-(D-Asp-β-Ala-D-Val-Leu-D-Trp); cyclo(D-Asp-Pro-D-Thg-Leu-D-Trp); cyclo(D-Asp-Thz-D-Val-Leu-D-Trp); cyclo(D-Asp-Pro-D-Val-MeLeu-D-Trp); cyclo(D-Asp-MeMet-D-Val-Leu-D-Trp); cyclo(D-Asp-Sar-D-Thg-Leu-D-Trp); cyclo(D-Asp-CpGly-D-Thg-Leu-D-Trp); cyclo(D-Asp-Pro-D-Dpg-Leu-D-Trp); cyclo(D-Cys($O_3$Na)-Pro-D-Thg-Leu-D-Trp(CHO)); cyclo(D-Cys($O_3$Na)-Pro-D-Thg-Leu-D-Trp); cyclo(D-Asp-Met($O_2$)-D-Val-Leu-D-Trp (CHO)); cyclo(D-Asp-PrGly-D-Thg-Leu-D-Trp); cyclo(D-Asp-trans-Hyp-D-Thg-Leu-D-Trp); cyclo(D-Asp-Pro-D-Fug-Leu-D-Trp); cyclo(D-AspoPro-D-Cpg-Leu-D-Trp); cyclo(D-Asp-Pro-D-Etg-Leu-D-Trp); cyclo(D-Asp-CmGly-D-Thg-Leu-D-Trp); cyclo(D-Asp-Pro-D-Val-His-D-Trp); cyclo(D-Asp-IeGly-D-Val-Leu-D-Trp); cyclo(D-Asp-Pro-D-Val-Leu-D-TrP(COO$CH_3$)); cyclo(D-AsP-Pro-D-Val-Leu-D-Trp(COO$^t$Bu)); cyclo(D-Asp-Pro-D-Val-Leu-D-Trp (O)); cyclo(D-Asp-MeAla-D-Val-Leu-D-Trp(O)); cyclo(D-Asp-Pro-D-Val-Leu-D-Trp($CH_2$OO$CH_3$)); cyclo(D-Asp-Pro-D-Val-Leu-D-Trp-($CH_2$CON$H_2$)); cyclo(D-Asp-Pro-D-Val-Leu-D-Trp($CH_2$CONH$CH_3$)); cyclo(D-Glu-Ala-D-Val-Leu-D-Nal); cyclo(D-Asp-trans-Hyp-D-Cpg-Leu-D-Trp); cyclo(D-Asp-Pro-D-Val-Leu-D-TrP($CH_2$COOH)); cyclo(D-Asp-Ala-D-Val-$C_6$al-D-Trp); cyclo(D-Asp-Pro-D-Val-Leu-D-Phe); nor cyclo(D-Asp-Pro-D-Val-Leu-D-Tyr).

Among the cyclic peptides that are provided herein are those that have formula (I):

$$\text{cyclo}(X^1\text{-}X^2\text{-}X^3\text{-}X^4\text{-D-Trp}) \quad (I)$$

or pharmaceutically acceptable salts, esters and other derivatives of the peptides, in which $X^1$ is D-Tyr or D-Asp; $X^2$ is Phe, Ala, $Ac_3c$ or Pro; $X^3$ is D-His, D-Ala, D-Val, Gly or β-Ala; and $X^4$ is D-His, His, Ala, β-Ala, Aib, Gly, D-His-gly or Leu, with the proviso that if $X^1$ is D-Asp, then either $X^2$ is $Ac_3c$ or $X^3$ is not $X^3$ is not D-Ala or D-Val, are provided. Preferred among these peptides are those in which $X^2$ is $Ac_3c$, and particularly those in which $X^3$ is D-Val, D-His, or D-Ala, and more preferably D-Val.

Cyclic pentapeptides and hexapeptides of formula (II):

$$\text{cyclo}(X^1\text{-L-Phe-}X^3\text{-}X^4\text{-}X^5), \quad (II)$$

or pharmaceutically acceptable salts, esters and other derivatives of the peptides, in which $X^1$ is D-Tyr, D-Asp or D-Glu, $X^3$ is selected from among D-His, β-Ala-D-His or gly-D-His; $X^4$ is Ser, Gly or β-Ala, and $X^5$ is D-Trp or N-Me-D-Trp are also provided. $X^3$ can also be L-His.

Preferred peptides of formula II include those in which $X^1$ is D-Tyr, D-Asp or D-Glu, preferably D-Tyr. Other preferred peptides are those in which $X^3$ is D-His. These peptides include cyclo(X-L-Phe-D-His-β-Ala-D-Trp) and cyclo(X-L-Phe-D-His-Gly-N-Me-D-Trp) in which X is D-Tyr or D-Asp. In order to increase the solubility of the above cyclic peptides the Gly and β-Ala may be replaced by serine.

Among the L-Trp-containing cyclic peptides provided herein are those that have formula (III):

$$\text{cyclo}(X^1\text{-}X^2\text{-}X^3\text{-}X^4\text{-L-Trp}) \quad (III)$$

and pharmaceutically acceptable salts and esters and other derivatives thereof that have the structure D-$X^1$-D-$X^2$-L-$X^3$-D-$X^4$-L-Trp in which $X^1$ is D-Ala, Aib, Gly, D-Val, D-Leu, D-Ile, D-Nva, D-Nle, or D-Alle; $X^2$ is D-Val, D-Leu, D-Ile, D-Ala, D-Gln, Gly, Aib, D-Nva, D-Nle, or D-Alle; $X^3$ is L-Pro, Gly, Aib, L-Val, L-Leu, L-Nva, L-Nle, L-Alle or L-Hyp and $X^4$ is D-Asp, D-Glu, D-Ser, D-Thr, D-Tyr, D-Cys($O_3$H) or D-Pen($O_3$H) are provided.

Preferred cyclic peptides of formula (III) or pharmaceutically acceptable salts, esters and other derivatives of the peptides include those in which $X^1$ is D-Ala, Aib, or Gly; $X^2$ is D-Val, D-Leu, D-Ile, D-Ala or D-Gln; and $X^4$ is D-Asp, D-Glu or D-Ser.

In addition, cyclic peptides that have the structure D-$X^1$-L-$X^2$-D-$X^3$-L-$X^4$-L-Trp and that have formula (IV):

$$\text{cyclo}(X^1\text{-}X^2\text{-}X^3\text{-}X^4\text{-L-Trp}) \quad (IV)$$

or pharmaceutically acceptable salts and esters and other pharmaceutically acceptable derivatives thereof in which $X^1$ is D-Leu, D-Val, D-Ile, D-Ala, Gly, Aib, D-Nva, D-Nle or D-Alle; $X^2$ is Val, Ile, Leu, Ala, Gln, Gly, Aib, L-Nva, L-Nle or L-Alle; $X^3$ is D-Pro, D-Hyp, D-Ala, D-Val, D-Ile, Gly, Aib, D-Nva, D-Nle or D-Alle; and $X^4$ is L-Asp, L-Glu, L-Tyr, L-Ser, L-Thr, L-Cys($O_3$H) or L-Pen($O_3$H) are provided.

Preferred among the peptides of formula (IV) or pharmaceutically acceptable salts, esters and other derivatives of the peptides are those in which $X^1$ is D-Leu, D-Val, D-Ile, or D-Ala; $X^2$ is Val, Ile, Leu or Ala; $X^3$ is D-Pro, D-Ala, D-Val or D-Ile; and $X^4$ is L-Asp, L-Glu, L-Tyr or L-Ser are provided. Peptides of formulas: cyclo(D-Leu-L-Val-D-Pro-L-Asp-L-Trp); cyclo(D-Leu-L-Val-D-Pro-L-Tyr-L-Trp); and cyclo(D-Leu-L-Val-D-Pro-L-Ser-L-Trp) are among the preferred peptides of formula (IV).

Preferred among the cyclic peptides provided herein, are those of the above peptides of formulas (I)–(IV) that inhibit the interaction of endothelin-1 with $ET_A$ receptors or $ET_B$ at an $IC_{50}$ of less than about 150 µM, and preferably less than about 100 µM and more preferably, less than about 50 µM.

Also among the preferred peptides are those that bind to $ET_A$ receptors at a lower concentration, preferably at least 2-fold lower, than they bind to $ET_B$ receptors. Also preferred among the cyclic peptides are those that bind to $ET_B$ receptors at the substantially the same or a lower concentration, preferably at least 2-fold lower, than they bind to $ET_A$ receptors.

The cyclic peptides can be used in methods for identification and isolation of specific endothelin receptors and in aiding in delineating the structure, function and biological activities mediated by endothelin. The peptides also should have use in pharmaceutical compositions as obstetric agents, including promoting closure of umbilical vessels, contraceptive agents, agents for the treatment of menstrual disorders, including amenorrhea and dysmenorrhea, wound healing agents, agents for the physiological regulation of blood pressure and treatment of vascular disorders, agents for neuroendocrine regulation, agents for treatment of cardiovascular diseases, and as agents for the treatment of other diseases listed herein and known to involve an endothelin peptide.

Pharmaceutical compositions containing effective concentrations of one or more of the cyclic peptides, or pharmaceutically acceptable salts or esters of the peptides, for the treatment of hypertension, bronchoconstriction, asthma, shock, ocular hypertension, cardiovascular disease, menstrual disorders, wounds, glaucoma and other conditions that are in some manner mediated by an endothelin peptide or that involve vasoconstriction are also provided.

In particular, the compositions contain therapeutically effective concentrations of one or more of the cyclic peptides of formulas (I), (II), (III) and (IV) formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, endotoxin shock, anaphylactic shock, hemorrhagic shock, and other diseases in which endothelin mediated physiological responses are implicated are provided.

Methods for altering endothelin receptor-mediated activity by contacting endothelin receptors with one or more of the cyclic peptides are provided.

Methods for treating endothelin-mediated disorders, including hypertension, cardiovascular diseases, cardiac diseases including myocardial infarction, pulmonary hypertension, erythropoietin-mediated hypertension, respiratory diseases and inflammatory diseases, including asthma, bronchoconstriction, ophthalmologic diseases, gastroenteric diseases, renal failure, ischemia, menstrual disorders, obstetric conditions, wounds, anaphylactic shock, hemorrhagic shock, and other diseases in which endothelin mediated physiological responses are implicated, by administering effective amounts of the compositions are also provided.

In particular, methods of treatment of these diseases, including hypertension, asthma, shock, ocular hypertension, glaucoma, menstrual disorders, obstetric conditions and other conditions or disorders that are in some manner mediated by an endothelin peptide or that involve vasoconstriction, by administering an effective amount of the pharmaceutical compositions that contain effective concentrations of one or more of the cyclic peptides of formulas (I)–(IV), or pharmaceutically acceptable salts or esters of the peptides, are provided. The effective amounts and concentrations are effective for ameliorating any of the symptoms of the any of the disorders. Preferred methods of treatment are methods for treatment of hypertension and renal failure.

In practicing these methods, effective amounts of compositions containing therapeutically effective concentrations of the cyclic peptides formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, ischemia, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods using the cyclic peptides for the identification and isolation of endothelin receptor subtypes are also provided. In particular, methods for detecting, distinguishing and isolating endothelin receptors using the cyclic peptides of formulas (I), (II), (III) and (IV) are provided. In practicing the method for identifying endothelin receptors, one or more of the cyclic peptides is linked to a support and used in methods of affinity purification of receptors. By selecting the cyclic peptides with particular specificities, distinct subclasses of endothelin receptors may be identified.

Methods for inhibiting the binding of an endothelin peptide to endothelin$_A$ ($ET_A$) or endothelin$_B$ ($ET_B$) receptors by contacting the receptors with an endothelin peptide and with one or more of the cyclic peptides in which the contacting is effected prior to, simultaneously with or subsequent to contacting the receptors with the endothelin peptide, are provided.

In addition, methods for identifying compounds that are suitable for use in treating particular diseases based on their preferential affinity for a particular endothelin receptor subtype are also provided.

Articles of manufacture containing packaging material, a peptide provided herein, which is effective for ameliorating the symptoms of an endothelin-mediated disorder, antagonizing the effects of endothelin or inhibiting binding of an endothelin peptide to an ET receptor with an $IC_{50}$ of less than about 100 µM, within the packaging material, and a label that indicates that the compound or salt thereof is used for antagonizing the effects of endothelin, treating an endothelin-mediated disorder, or inhibiting the binding of an endothelin peptide to an ET receptor are provided.

BRIEF DESCRIPTION OF THE FIGURE

FIGS. 1A–1F set forth the X, Y, Z coordinates of residues 13–21 of endothelin-1.

DETAILED DESCRIPTION OF THE PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or is a condition, disease or disorder in which compounds that inhibit endothelin activity ameliorate the symptoms of the condition, disease or disorder. Such conditions, diseases and disorders include, but are not limited to hypertension, cardiovascular disease, asthma, inflammatory diseases, ophthalmologic disease, menstrual disorders, obstetric conditions, gastroenteric disease, renal failure, pulmonary hypertension, ischemia, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" Eur. J. Pharmacol. 165: 223–230). Endothelin antagonist activity can be assessed by the ability to interfere with endothelin-induced vasoconstriction.

As used herein, the biological activity or bioactivity of endothelin includes any activity induced, potentiated or influenced by endothelin in vivo. It also includes the ability to bind to particular receptors and to induce a functional response, such as vasoconstriction. It may be assessed by in vivo assays or by in vitro assays, such as those exemplified herein. The relevant activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction. Any assay known to those of skill in the art to measure or detect such activity may be used to assess such activity (see, e.,q., Spokes et al. (1989) J. Cardiovasc. Pharmacol. 13(Suppl. 5):S191–S192; Spinella et al. (1991) Proc. Natl. Acad. Sci. USA 88: 7443–7446; Cardell et al. (1991) Neurochem. Int. 18:571–574); and the Examples herein).

As used herein, the $IC_{50}$ refers to an amount, concentration or dosage of a particular test compound that achieves a 50% inhibition of a maximal response, such as binding of endothelin to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a peptidomimetic is a compound that mimics the conformation and certain stereochemical features of the biologically active form of a particular peptide. In general, peptidomimetics are designed to mimic certain desirable properties of a compound, but not the undesirable properties, such as flexibility, that lead to a loss of a biologically active conformation and bond breakdown. Peptidomimetics may be prepared from biologically active compounds by replacing certain groups or bonds that contribute to the undesirable properties with bioisosteres. Bioisosteres are known to those of skill in the art (see, e.q., U.S. Pat. No. 5,331,573). For example the methylene bioisostere $CH_2S$ has been used as an amide replacement in enkephalin analogs (see, e.g., Spatola (1983) pp. 267–357 in Chemistry and Biochemistry of Amino Acids, Peptides, and Proteins, Weistein, Ed. volume 7, Marcel Dekker, New York). Morphine, which can be administered orally, is a compound that is a peptidomimetic of the peptide endorphin.

As used herein, a non-peptidic compound refers to compounds that do not include more than two linked amino acids and that include linkages other than peptide bonds among the constituent groups.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, treatment means any manner in which the symptoms of a condition, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392).

As used herein, hydrophobic amino acids include Ala, Val, Leu, Ile, Pro, Phe, Trp, and Met and any other non-naturally occurring amino acids, including as the corresponding D isomers of the hydrophobic amino acids, that have similar hydrophobic properties. It is also understood that certain amino acids may be replaced by substantially equivalent non-naturally occurring variants thereof, such as D-Nva, D-Nle, D-Alle, and others listed with the abbreviations below or known to those of skill in this art.

As used herein, the abbreviations for amino acids and protective groups are in accord with their common usage and the IUPAC-IUB Commission on Biochemical Nomenclature (see, (1972) *Biochem.* 11:1726). Each naturally occurring L-amino acid is identified by the standard three letter code or the standard three letter code with or without the prefix "L-"; the prefix "D-" indicates that the stereoisomeric form of the amino acid is D. Other abbreviations used herein include: Aib for 2-amino-2-methylpropionic acid; β-Ala for β-alanine, α-Aba for L-α-aminobutanoic acid; D-α-Aba for D-α-aminobutanoic acid; $Ac_3c$ for 1-aminocyclopropanecarboxylic acid; $Ac_4c$ for 1-aminocyclobutanecarboxylic acid; $Ac_5c$ for 1-aminocyclopentanecarboxylic acid; $Ac_6c$ for 1-aminocyclohexanecarboxylic acid; $Ac_7c$ for 1-aminocycloheptanecarboxylic acid; D-Asp(ONa) for sodium D-aspartate; D-Bta for D-3-(3-benzo[b]thienyl)alanine; $C_3$al for L-3-cyclopropylalanine; $C_4$al for L-3-cyclobutylalanine; $C_5$al for L-3-cyclopentylalanine; $C_6$al for L-3-cyclohexylalanine; D-Chg for D-2-cyclohexylglycine; CmGly for N-(carboxymethyl)glycine; D-Cpg for D-2-cyclopentylglycine; CpGly for N-cyclopentylglycine; Cys($O_3$Na) for sodium L-cysteate; D-Cys($O_3$H) for D-cysteic acid; D-Cys($O_3$Na) for sodium D-cysteate; D-Cys($O_3Bu_4$N) for tetrabutylammonium D-cysteate; D-Dpg for D-2-(1,4-cyclohexadienyl)-glycine; D-Etg for (2S)-2-ethyl-2-(2-thienyl)glycine; D-Fug for D-2-(2-furyl)glycine; Hyp for 4-hydroxy-L-proline; IeGly for N-[2-(4-imida-zolyl)ethyl]glycine; alle for L-alloisoleucine; D-alle for D-alloisoleucine; D-Itg for D-2-(isothiazolyl)glycine; D-tertLeu for D-2-amino-3,3-dimethylbutanoic acid; Lys (CHO) for $N^6$-formyl-L-lysine; MeAla for N-methyl-L-alanine; MeLeu for N-methyl-L-leucine; MeMet for N-methyl-L-methionine; Met(O) for L-methionine sulfoxide; Met($O_2$) for L-methionine sulfone; D-Nal for D-3-(1-naphthyl)alanine; Nle for L-norleucine; D-Nle for D-norleucine; Nva for L-norvaline; D-Nva for D-norvaline; Orn for L-ornithine; Orn(CHO) for $N^5$-formyl-L-ornithine; D-Pen for D-penicillamine; D-Phg for D-phenylglycine; Pip for L-pipecolinic acid; $^i$PrGly for N-isopropylglycine; Sar for sarcosine; Tha for L-3-(2-thienyl)alanine; D-Tha for D-3(2-thienyl)-alanine; D-Thg for D-2-(2-thienyl)glycine; Thz for L-thiazolidine-4-carboxy-lic acid; D-Trp(CHO) for $N^{in}$-formyl-D-tryptophan; D-trp(O) for D-3-(2,3-di-hydro-2-oxoindol-3-yl)alanine; D-trp(($CH_2$)$_m COR^1$) for D-tryptophan substituted by a —($CH_2$)$^m COR^1$ group at the 1-position of the indole ring; Tza for L-3-(2-thiazolyl)alanine; D-Tza for D-3-(2-thiazolyl)alanine; D-Tzg for D-2-(thiazolyl)glycine; Bzl for benzyl; DMF for N,N-dimethylformamide; Boc for tert-butoxycarbonyl; TFA for trifluoroacetic acid; HF for hydrogen fluoride; HFIP for hexafluoroisopropanol; HPLC for high performance liquid chromatography; FAB-MS for fast atom bombardment mass spectrometry; DCM is dichloromethane, Bom is benzyloxymethyl; Pd/C is palladium catalyst on activated charcoal; BOP is benzotriazol-1-yloxy-tris(dimethylamino) phosphonium hexafluorophosphate; DIC is diisopropylcarbodiimide; DCC is N,N'-dicyclohexylcarbodiimide; and (For)is formyl.

Rational Design of Compounds that Mimic the Surface Features of Endothelin

The cyclic peptides that mimic surface features of endothelin were designed using the rational method of drug design described in detail in copending U.S. application Ser. No. 08/223,513 and U.S. Pat. No. 5,331,573. This method for design of the cyclic peptides involved the following steps:

(A) simulating the most probable conformations of endothelin-1 and selecting the most probable conformation from among the simulated conformations;

(B) designing and synthesizing cyclic peptides that mimic selected surface features of the three-dimensional structure of endothelin-1; and (C) evaluating the bioactivity of the cyclic peptides.

(A) Simulating the most probable conformations and selecting the most probable conformation from among those simulated The first step in designing the cyclic peptides that mimic surface features of endothelin-1 required simulation of the most probable conformations of the target polypeptide endothelin-1. This was accomplished using the ab initio method described in copending U.S. application Ser. No. 08/223,513 and U.S. Pat. No. 5,331,573. Briefly, the ab initio process involved: (a) simulating a real-size primary structure of a polypeptide in a solvent box, typically an aqueous environment; (b) shirking the size of the peptide isobarically and isothermally; and (c) expanding the peptide to and beyond its real size in selected time periods, while measuring the energy state and coordinates, e.g., the $\phi$ and $\psi$ angles, of the expanding molecule(s).

The most probable conformation of endothelin-1 was simulated in an IBM RS6000/550 model computer using a data set and the simulation program described in copending U.S. application Ser. No. 08/223,513 and U.S. Pat. No. 5,331,573. Initial data entry into the program required specifying the amino acids in the endothelin-1 peptide chain, specifying that the length of the endothelin-1 is twenty-one amino acids, and specifying that the simulation medium is an aqueous medium. The location of the disulfide bridges were also specified. In this case, it was specified that the side chains of the $Cys^3$ and $Cys^{11}$ and the $Cys^1$ and $Cys^{15}$ were bridged. The simulation data was organized according to each amino acid residue of the peptide chain and compared with a data set containing amino acids and other non-naturally occurring amino acids.

After initial data entry into the computer simulation program, specifying the number of residues in the primary peptide structure and the particular amino acid represented by each residue, the appropriate data set for the specified residue was retrieved by the simulation program. The requisite parameters for each residue were then entered into the program. The data set for each amino acid includes the values of the $\phi$, $\psi$ angles that orient the amide planes of each residue relative to the $C^\alpha$ atom of the residue. Chemical and physical data associated with any pendant groups (or side chains) of the peptide were also entered into the simulation program. Physical data associated with each atom and/or group of atoms, including bond lengths and electrical forces associated with the particular atom and/or molecule, are well documented in the literature (see, e.g., Weiner et al. (1986) *J. Comput. Chem.* 7: 230–252; Weiner et al. (1984) *J. Am. Chem. Soc.* 106: 7052–7067).

Having defined the background solvent and peptide chain, the various molecules present in the endothelin chain were permitted to interact with each other in accordance with the normal electrical and/or molecular forces present within such molecules represented by the total potential energy of the molecule. The total potential energy of the molecule was calculated as described by Ramnarayan et al. ((1990) *J. Chem Phys.*, 92:7052–7067) using parameters described by Weiner et al. ((1986) *J. Comput. Chem.* 7:230–252) according to the Equation (2):

$$V_{total} = \sum_{bonds} \frac{K_r}{2}(r - r_{eq}) + \sum_{angles} \frac{K_\theta}{2}(\theta - \theta_{eq})^2 + \sum_{dihedrals} \frac{V_n}{2}[1 + \cos(n\phi - \gamma)] + \sum_{i<j}\left[\frac{A_{ij}}{R_{ij}^{12}} - \frac{B_{ij}}{R_{ij}^6} + \frac{q_iq_j}{\epsilon R_{ij}}\right] + \sum_{H\ bonds}\left[\frac{C_{ij}}{R_{ij}^{12}} - \frac{D_{ij}}{R_{ij}^{10}}\right] - \sum_i\sum_j q_i \frac{\bar{\mu}_j \cdot \hat{r}_{ij}}{r_{ij}^3} + \sum_{i>j}\bar{\mu}_j\nabla\left[\frac{\bar{\mu}_i \cdot \bar{r}_{ij}}{r_{ij}^3}\right] + \sum_j \frac{1}{2}\alpha_j E_j^2,$$

which includes the contribution of various components of a system of N atoms to the total potential energy. The first term in Equation (2) represents the strain energy associated with the variation of the bond length r from its equilibrium value $r_{eq}$, and $K_r$ represents the force constant associated with the deformation. The second term represents the contribution from the energy due to the deformation of the bond angle $\theta$ from its equilibrium value $\theta_{eq}$, with a force constant of deformation $K_\theta$. The third term is the torsional energy resulting from bond rotation in which $V_n$ is the barrier to rotation ($\phi$) about a phase angle of $\gamma$. The fourth term is the nonbonded energy of the system including the 6–12 potential and electrostatic energy according to Coulombs law and the fifth term is a 10–12 potential that represents the hydrogen bonds in the force field. The last three terms are the contribution of the total polarization energy for a system of charges and dipoles in which $q_i$ is the charge of the ith atom and $\bar{\mu}_i$ is the induced dipole moment of the ith atom, where $\bar{\mu}_i = \alpha_i E_i$ in which $\alpha_i$ is the atomic polarizability of the ith atom and $E_i$ is the electric field at this atom.

The bond lengths between the various ions, atoms and molecules of each residue were defined and the amino acid residues arranged along relatively rigid amide planes that are joined to $C^\alpha$ atoms at "swivel points".

To assure that the most probable conformation was identified, a shrinking and growing process was invoked in which the initial bond lengths in the peptide chain backbone included in the respective amino acid data sets were scaled down by 5% of their normal size. The bond lengths associated with the background solvent were maintained at their normal sizes. With the bond lengths reduced by the specified size factor, a "modified molecular mechanics" simulation was invoked. The scaling down of the bond lengths was carried out both isobarically and isothermally. With the scaling down of the bond lengths, the ambient pressure and temperature values used while performing the molecular mechanics simulation were also scaled down accordingly.

In the first cycle, which involved thirty-five computer clock hours, the molecular forces associated with the then current position of the peptide molecules were computed. In accordance with known dynamics, these forces interacted with the molecule to begin to move or change the current position of the molecules to a new position. In a second cycle, the same calculations were recomputed in order to determine the forces associated with the new position of the peptide molecules based on their new position, which forces interact to move the molecules to another position. The iterative process was continued until the energy change between cycles was less than 0.001 Kcal/mol. This iterative process in which the dynamics of the shrinking and expanded of the endothelin-1 structure were ascertained, produced data from which Balaji plots were generated.

The Balaji plot is a refinement or modification of a "Balasubramanian Plot" (see Balasubramanian, R. (1974) "New Type of Representation for Mapping Chain Folding in Protein Molecules" *Nature* 266: 856–857), which represents the values of the $\phi$, $\psi$ angles of each residue of a polypeptide chain as solid dots and open circles, respectively, connected by a vertical line. The Balasubramanian plot uses a vertical angular axis, and a horizontal residue number axis. In a Balasubramanian plot, the peptide is depicted as a series of different vertical lines, each having solid dots and open circles aligned with the corresponding $\phi$, $\psi$ angle values on the vertical axis, and where each line corresponds to the particular number of the residue having the plotted $\phi$, $\psi$ angles as indicated on a horizontal axis. In the Balaji plot, the values of the $\phi$, $\psi$ angles are shown as the base and tip of a vertical wedge (assuming a vertical angular axis), respectively, with a separate wedge being horizontally positioned on the plot as a function of the residue number of the φ, ψ angles plotted. The Balaji plot replaces the solid dots and open circles of the Balasubramanian Plot with the base of a wedge and the tip of a wedge, respectively; and further replaces the vertical line joining the dots and open circles of the Balasubramanian plot with the body of the wedge.

The stimulated endothelin molecules remained at the scaled down size for three hundred picoseconds, and underwent the changes in conformation resulting from the modified molecular mechanics simulation during the prescribed period of time. At the conclusion of this time, the molecule was at its normal size and the ab initio growth process was terminated. When terminated, the final φ, ψ angles, were recorded and used during the next step of the drug design method.

Using the simulation method of shrinking the polypeptide in a solvent box and expanding it to and beyond its normal size, Balaji plots showing the φ, ψ angles or the changes in the φ, ψ angles of the numerous residues in endothelin-1 that exhibit propensity for change were generated. This information provided insights into the manner in which endothelin folds or otherwise arranges its various residues in a complex conformation. Predicted tertiary structures of endothelin-1, that represent the most probable structures were thereby determined and the most probable conformation was then selected from among the predicted structures. The coordinates of the most probable conformation of the C-terminal portion of endothelin-1 are set forth in FIG. 1.
(B) Design and synthesis of cyclic peptides that mimic selected surface features of endothelin-1

(1) Design of the cyclic peptide surface feature mimics

The next step involved designing and synthesizing cyclic peptides that mimic selected surface features of the simulated three-dimensional structure of endothelin-1 using the method described in copending U.S. application Ser. No. 08/223,513. In general, designing and synthesizing a chemically modified analog involves using the sequence of the peptide and the conformation data to determine the geometries that should be designed into the chemically modified analog.

Copending U.S. application Ser. No. 08/223,513 and U.S. Pat. No. 5,331,573 also provide a refined protocol for obtaining conformational energy maps, a compilation of conformational features of several model dipeptide analogs and includes a compilation of conformational features of several model oligopeptides. These features were used in searching for and designing cyclic peptide analogs that mimic surface features of endothelin-1.

In order to limit the number of cyclic peptides, information regarding the relative importance of certain portions of the molecule, such as the $Trp^{21}$ residue, was used in selecting the regions of endothelin-1 to mimic. Using available structure activity relationships and stimulated structure that correspond to modified endothelin peptides, the surface corresponding to the C-terminal portion, encompassing roughly residues 13–21, selected as described below, of endothelin-1 was selected as the region on which to model the cyclic peptides.

Computer simulations of the structures of endothelin analogs demonstrated that elimination of the two disulfide bridges results in a molecule with a completely different shape from native endothelin-1. Simulated three-dimensional structures were also generated for endothelin-1 in which the disulfide bonds are formed between residues $Cys^1$–$Cys^{11}$ and between $Cys^3$–$Cys^{15}$. Such structures exhibit some endothelin activity. The endothelin-1 structure which exhibits a marked decrease in activity, in which the disulfide bonds are formed between the $Cys^1$ with the $Cys^3$ and the $Cys^{11}$ with the $Cys^{15}$ was also simulated. The three-dimensional structures of these molecules were examined and compared with the structure of endothelin-1 and the structure of endothelin-1 in which the disulfide bonds are eliminated in order to determine which surface features remain constant and which are altered.

The simulated surfaces were compared. The features common to all four surfaces were not of interest because a region in common among the four forms is not likely to be important for activity. The regions that the active structures do not have in common with the inactive ones may be important. Similarly, the three-dimensional structure of the endothelin analogs, in which the disulfide bridge is replaced with a peptide bond and which exhibits decreased activity, was generated. The resulting conformation differs from that of native endothelin-1.

Data obtained from an L-Ala scan was considered (see, Castiglinone et al. (1991) in *Peptides: Chemistry and Biology*, Proc. Amer. Pept. Symp. (Twelfth) J. A. Smith and J. E. Rivier, Eds., ESCOM, Leiden, pp. 402–403). For example, if the $Trp^{21}$ is replaced with L-Ala, the resulting analog lacks activity (see, also, Kimura et al. (1989) *Biochem. Biophys. Res. Commun.*, 156:1182–1186; Hirata et al. (1989) *Biochem. Biophys. Res. Commun.*, 160:228–234). If the $His^{16}$ is replaced with L-Ala, the vasoconstrictor activity increases, indicating that the His plays a role in the active site. The data from the alanine scan also suggests that the $Asp^8$ residue appears to be important even though it is at least 6 to 7 angstroms from $Trp^{21}$. Based on this data, the data obtained from comparison of the simulated surfaces, and other such data, it has been determined that the residues of endothelin-1 that are important for activity include the $Tyr^{13}$, $Phe^{14}$, $His^{16}$, $Leu^{17}$ and $Trp^{21}$ residues.

Using the ab initio protocol described in copending U.S. application Ser. No. 08/223,513 and U.S. Pat. No. 5,331,573, all possible conformers for five to seven membered cyclic peptides containing both L and D residues were generated. For each of these cyclic peptides, the values of the backbone side chain orientation were compared to the backbone side chain orientation of the C-terminal portion of endothelin-1 and those showing more than 60% of goodness of fit, set forth in Equation (1), above, were chosen for further design.

Having selected the best fitting cyclic peptides according to the criteria defined above, the selected cyclic peptides were modified by replacing the alanyl side chains with appropriate side chains determined by superimposition of the cyclic peptide on the three-dimensional structure of the C-terminal portion of endothelin-1. In particular, to design cyclic peptide surface feature mimics of endothelin-1, the structure of a number cyclic pentapeptides, cyclic hexapeptides and cyclic heptapeptides containing combinations of L-Ala, and D-Ala residues were simulated using the ab initio methods and those that best match the surface of endothelin-1 in the region of the C-terminus that includes the $Tyr^{13}$, $Phe^{14}$, $His^{16}$, $Leu^{17}$ and $Trp^{21}$ residues were generated.

The cyclic peptides were generated using a data base containing a set of cyclic peptide structures with only alanine as a side chain using all permutations of various combinations of five, six and seven Ala residues, including D- and L-Ala. The cyclic peptides in the data base have been superimposed on the simulated three-dimensional structure of endothelin-1 by superimposing the cyclic peptides on the coordinates of endothelin-1 and selecting the best fits to the region that includes the $Trp^{21}$ terminus. Best matches were selected using the "goodness of fit" equation as described above.

Depending upon the stringency of the parameters, two Ala cyclic peptide backbone structures cyclo(D-Ala-L-Ala-D-Ala-L-D-Ala) and cyclo(D-Ala-L-Ala-D-Ala-L-Ala-L-Ala) were selected for further investigation. In a like manner additional cyclic peptides containing six or seven Ala residues (cyclic hexapeptides and cyclic heptapeptides) may be selected.

Each group of Ala-based cyclic peptides were selected for further modification by superimposing peptide structures on the structures of endothelin in order to assess what endothelin residues were not covered by the cyclic peptide. Residues with chains beyond the carbon atom will not be covered upon superimposition of the Ala-based cyclic peptide. Modifications of the Ala backbone which mimic these extending chains were introduced. L-Trp and D-Trp residues were introduced into each of the selected group of peptides.

The resulting first group includes peptides that have the cyclic peptide backbone cyclo(D-Ala-L-Ala-D-Ala-L-Ala-D-Ala) and include a D-Trp residue in place of a D-Ala residue. A second and third have either the backbone cyclo(D-Ala-L-Ala-D-Ala-L-Ala-D-Ala) and cyclo(D-Ala-L-Ala-D-Ala-L-Ala-L-Ala), respectively and include an L-Trp in place of an L-Ala. Each group was then superimposed on the C-terminal region of endothelin and the remaining residues were matched with the surface features to generate several series of cyclic peptides that mimic surface features of endothelin-1. Cyclic peptides that mimic surface features of the C-terminal portion of endothelin-1, represented by the coordinates set forth in FIG. 1, were, thus, designed.

The cyclic peptides, or pharmaceutically acceptable salts, esters or other derivatives of the peptides, contain between 5 and 7 residues that match the surface features of the C-terminal portion of endothelin-1 are provided. The residues of the cyclic peptides are selected such that the peptides have a goodness of fit as defined by Equation (1) of at least about 60% with the coordinates, which are set forth in FIG. 1, of the C-terminal region of endothelin; provided that $X^1$, $X^2$, $X^3$, $X^4$ are selected such that:

(i) if the peptide is a cyclic pentapeptide it has the structure, in which the designations D- and L- refer to the stereochemistry of the amino acid residue and the superscripts referring to the positions of the residue relative to the specified Trp residue if the cyclic peptide is opened and the Trp is at the end, D-$X^1$-L-$X^2$-D-$X^3$-L-$X^4$-D-Trp, D-$X^1$-D-$X^2$-L-$X^3$-D-$X^4$-L-Trp, D-$X^1$-L-$X^2$-D-$X^3$-D-$X^4$-D-Trp, D-$X^1$-L-$X^2$-D-$X^3$-L-$X^4$-L-Trp, with D-$X^1$-L-$X^2$-D-$X^3$-L-$X^4$-D-Trp, D-$X^1$-D-$X^2$-L-$X^3$-D-$X^4$-L-Trp or D-$X^1$-L-$X^2$-D-$X^3$-L-$X^4$-L-Trp preferred, or the peptide includes an amino acid or amino acid that is not optically active in place of one or more of $X^1$–$X^4$;

(ii) if the structure is D-$X^1$-L-$X^2$-D-$X^3$-L-$X^4$-D-Trp, then residue $X^2$ is not L-Trp;

(iii) if the peptide is a cyclic heptapeptide or cyclic hexapeptide, it has any of the backbones set forth in (i), but with an additional one or two residues inserted therein; and (iv) it is not selected from cyclo(D-Asp-Ala-D-Ala-Ala-D-Trp); cyclo(D-Asp-Pro-D-Val-Leu-D-Trp); cyclo(D-Glu-L-Ala-allo-D-Ile-L-Leu-D-Trp); cyclo(D-Glu-Ser-D-Val-Leu-D-Trp); cyclo(D-Cys(O$_3$Na)-Ala-D-Val-Leu-D-Trp); cyclo(D-Asp-Lys-D-Val-Leu-D-Trp); cyclo(D-Cys(O$_3$Na)-pro-D-Val-Leu-D-Trp); cyclo(D-Cys(O$_3$Na)-Pro-D-Val-Nle-D-Trp); cyclo(D-Asp-Leu-D-Val-Leu-D-Trp); cyclo(D-Glu-Ala-D-Val-Leu-D-Trp); cyclo(D-Glu-Ala-D-Alle-Leu-D-Trp); cyclo(D-Glu-Pro-D-Val-Leu-D-Trp); cyclo(D-Asp-Gly-D-Val-Leu-D-Trp); cyclo(D-Asp-Ala-D-Val-Leu-D-Trp); cyclo(D-Asp-Leu-D-Val-Leu-D-Trp); cyclo(D-Asp-MeAla-D-Val-Leu-D-Trp); cyclo(D-Asp-Met-D-Val-Leu-D-Trp); cyclo(D-Asp-Trp-D-Val-Leu-D-Trp); cyclo(D-Asp-His-D-Val-Leu-D-Trp); cyclo(D-Asp-Arg-D-Val-Leu-D-Trp); cyclo(D-Asp-Orn-D-Val-Leu-D-Trp); cyclo(D-Asp-Gln-D-Val-Leu-D-Trp); cyclo(D-Asp-Asp-D-Val-Leu-D-Trp); cyclo(D-Asp-Cys(O$_3$Na)-D-Val-Leu-D-Trp); cyclo(D-Asp-Cys-D-Val-Leu-D-Trp); cyclo(D-Asp-Ser-D-Val-Leu-D-Trp); cyclo(D-Asp-Thr-D-Val-Leu-D-Trp); cyclo(D-Asp-Ala-D-Leu-Leu-D-Trp); cyclo(D-Asp-Ala-D-Thr-Leu-D-Trp); cyclo(D-Asp-Pro-D-Ile-Leu-D-Trp); cyclo(D-Asp-Pro-D-Alle-Leu-D-Trp); cyclo(D-Asp-Pro-D-Nle-Leu-D-Trp); cyclo(D-Asp-Pro-D-Phg-Leu-D-Trp); cyclo(D-Asp-Pro-D-Nva-Leu-D-Trp); cyclo(D-Asp-Ser-D-Val-Nlle-D-Trp); cyclo(D-Asp-Ser-D-Val-Met-D-Trp); cyclo(D-Asp-Asp-D-Val-Ala-D-Trp); cyclo(D-Asp-Ala-D-Val-Pro-D-Trp); cyclo(D-Asp-Pro-D-Val-Ile-D-Trp); cyclo(D-Asp-Pro-D-Val-Nlle-D-Trp); cyclo(D-Cys(O$_3$Na)-Cys(O$_3$Na)-D-Val-Leu-D-Trp); cyclo(D-Cys(O$_3$Na)-Pro-D-Alle-Leu-D-Trp); cyclo(D-Asp-Val-D-Val-Leu-D-Trp); cyclo(D-Asp-Pro-D-Val-Nva-D-Trp); cyclo(D-Asp-Nlle-D-Val-Leu-D-Trp); cyclo(D-Asp-Pip-D-Val-Leu-D-Trp); cyclo(D-Asp-Phe-D-Val-Leu-D-Trp); cyclo(D-Cys(O$_3$Na)-Glu-D-Val-Leu-D-Trp); cyclo(D-Cys(O$_3$Na)-Lys-D-Val-Leu-D-Trp); cyclo(D-Asp-Pro-D-Val-Leu-D-Trp(CHO)); cyclo(D-Glu-Ala-D-Alle-Leu-D-Trp(CHO)); cyclo(D-Asp-Pro-D-Alle-Leu-D-Trp(CHO)); cyclo(D-Asp-Ser-D-Val-Nle-D-Trp(CHO)); cyclo(D-Asp-Met-D-Val-Leu-D-Trp(CHO)); cyclo(D-Asp-Pro-D-Val-Nva-D-Trp(CHO)); cyclo(D-Asp-Lys(CHO)-D-Val-Leu-D-Trp(CHO)); cyclo(D-Asp-Met(O)-D-Val-Leu-D-Trp(CHO)); cyclo(D-Asp(ONa)-Pro-DVal-Leu-D-Trp); cyclo(D-Asp-Pro-D-Pen-Leu-D-Trp); cyclo(D-Asp-Aib-D-Val-Leu-D-Trp); cyclo(D-Asp-Pro-Aib-Leu-D-Trp); cyclo(D-Asp-Pro-AC$_5$C-Leu-D-Trp); cyclo(D-Asp-Pro-AC$_6$C-Leu-D-Trp); cyclo(D-Asp-Sar-D-Val-Leu-D-Trp); cyclo(D-Asp-β-Ala-D-Val-Leu-D-Trp); cyclo(D-Asp-Pro-D-Thg-Leu-D-Trp); cyclo(D-Asp-Thz-D-Val-Leu-D-Trp); cyclo(D-Asp-Pro-D-Val-MeLeu-D-Trp); cyclo(D-Asp-MeMet-D-Val-Leu-D-Trp); cyclo(D-Asp-Sar-D-Thg-Leu-D-Trp); cyclo(D-Asp-CpGly-D-Thg-Leu-D-Trp); cyclo(D-Asp-Pro-D-Dpg.-Leu-D-Trp); cyclo(D-Cys(O$_3$Na)-Pro-D-Thg-Leu-D-Trp(CHO)); cyclo(D-Cys(O$_3$Na)-pro-D-Thg-Leu-D-Trp); cyclo(D-Asp-Met(O$_2$)-D-Val-Leu-D-Trp(CHO)); cyclo(D-Asp-PrGly-D-Thg-Leu-D-Trp); cyclo(D-Asp-trans-Hyp-D-Thg-Leu-D-Trp); cyclo(D-Asp-Pro-D-Fug-Leu-D-Trp); cyclo(D-Asp-Pro-D-Cpg-Leu-D-Trp); cyclo(D-Asp-Pro-D-Etg-Leu-D-Trp); cyclo(D-Asp-CmGly-D-Thg-Leu-D-Trp); cyclo(D-Asp-Pro-D-Val-His-D-Trp); cyclo(D-Asp-IeGly-D-Val-Leu-D-Trp); cyclo(D-Asp-Pro-D-Val-Leu-D-TrP(COOCH$_3$)); cyclo(D-Asp-Pro-D-Val-Leu-D-Trp(COO$^t$Bu)); cyclo(D-Asp-Pro-D-Val-Leu-D-Trp(O)); cyclo(D-Asp-MeAla-D-Val-Leu-D-Trp(O)); cyclo(D-Asp-Pro-D-Val-Leu-D-Trp(CH$_2$OOCH$_3$)); cyclo(D-Asp-Pro-D-Val-Leu-D-Trp(CH$_2$CONH$_2$)); cyclo(D-Asp-Pro-D-Val-Leu-D-Trp-(CH$_2$CONHCH$_3$)); cyclo(D-Glu-Ala-D-Val-Leu-D-Nal); cyclo(D-Asp-trans-Hyp-D-Cpg-Leu-D-Trp); cyclo(D-Asp-Pro-D-Val-Leu-D-Trp(CH$_2$COOH)); cyclo(D-Asp-Ala-D-Val-C$_6$al-D-Trp); cyclo(D-Asp-Pro-D-Val-Leu-D-Phe); or cyclo(D-Asp-Pro-D-Val-Leu-D-Tyr).

21

(a) D-Trp-containing cyclic peptides

Among the cyclic peptides that are provided herein are those that have formula (I):

cyclo($X^1$-$X^2$-$X^3$-$X^4$-D-Trp)  (I)

or pharmaceutically acceptable salts, esters and other derivatives of the peptides, in which $X^1$ is any amino acid, preferably a D-amino acid or amino acid that confers an equivalent conformation on the resulting cyclic peptide; $X^2$ is a hydrophobic amino acid, preferably an L-amino acid; $X^3$ is a hydrophobic D-amino acid, Gly, or β-Ala, and $X^4$ is a hydrophobic amino acid, preferably a D-amino acid, or is Ala, β-Ala, Aib, Gly, D-His-gly or Leu, provided that $X^1$, $X^2$, $X^3$ and $X^4$ are selected such that the peptide of formula (I) is:

(i) if the peptide of formula (I) is a cyclic pentapeptide, it has the structure D-$X^1$-L-$X^2$-D-$X^3$-L-$X^4$-D-Trp, D-$X^1$-L-$X^2$-D-$X^3$-D-$X^4$-D-Trp, with D-$X^1$-L-$X^2$-D-$X^3$-L-$X^4$-D-Trp preferred, the designations D- and L- refer to the stereochemistry of the amino acid residue as above, or it includes an amino acid or amino acid that is not optically active in place of one or more of $X^1$–$X^4$;

(ii) if the structure is D-$X^1$-L-$X^2$-D-$X^3$-L-$X^4$-D-Trp, then residue $X^2$ is not L-Trp;

(iii) if the peptide is a cyclic heptapeptide or cyclic hexapeptide, it has any of the backbones set forth in (i), but with an additional one or two residues inserted therein; and (iv) the selected the cyclic peptide is not any of the following peptides: cyclo(D-Asp-Pro-D-Val-Leu-D-Trp); cyclo(D-Glu-L-Ala-allo-D-Ile-L-Leu-D-Trp); cyclo(D-Cys-Glu-Ser-D-Val-Leu-D-Trp); cyclo(D-Cys($O_3$Na)-Ala-D-Val-Leu-D-Trp); cyclo(D-Asp-Lys-D-Val-Leu-D-Trp); cyclo(D-Cys($O_3$Na)-pro-D-Val-Leu-D-Trp); cyclo(D-Cys($O_3$Na)-pro-D-Val-Nle-D-Trp); cyclo(D-Asp-Leu-D-Val-Leu-D-Trp); cyclo(D-Glu-Ala-D-Val-Leu-D-Trp); cyclo(D-Glu-Ala-D-Alle-Leu-D-Trp); cyclo(D-Glu-Pro-D-Val-Leu-D-Trp); cyclo(D-Asp-Gly-D-Val-Leu-D-Trp); cyclo(D-Asp-Ala-D-Val-Leu-D-Trp); cyclo(D-Asp-Leu-D-Val-Leu-D-Trp); cyclo(D-Asp-MeAla-D-Val-Leu-D-Trp); cyclo(D-Asp-Met-D-Val-Leu-D-Trp); cyclo(D-Asp-Trp-D-Val-Leu-D-Trp); cyclo(D-Asp-His-D-Val-Leu-D-Trp); cyclo(D-Asp-Arg-D-Val-Leu-D-Trp); cyclo(D-Asp-Orn-D-Val-Leu-D-Trp); cyclo(D-Asp-Gln-D-Val-Leu-D-Trp); cyclo(D-Asp-Asp-D-Val-Leu-D-Trp); cyclo(D-Asp-Cys($O_3$Na)-D-Val-Leu-D-Trp); cyclo(D-Asp-Cys-D-Val-Leu-D-Trp); cyclo(D-Asp-Ser-D-Val-Leu-D-Trp); cyclo(D-Asp-Thr-D-Val-Leu-D-Trp); cyclo(D-Asp-Ala-D-Leu-Leu-D-Trp); cyclo(D-Asp-Ala-D-Thr-Leu-D-Trp); cyclo(D-Asp-Pro-D-Ile-Leu-D-Trp); cyclo(D-Asp-Pro-D-Alle-Leu-D-Trp); cyclo(D-Asp-Pro-D-Nle-Leu-D-Trp); cyclo(D-Asp-Pro-D-Phg-Leu-D-Trp); cyclo(D-Asp-Pro-D-Nva-Leu-D-Trp); cyclo(D-Asp-Ser-D-Val-Nlle-D-Trp); cyclo(D-Asp-Ser-D-Val-Met-D-Trp); cyclo(D-Asp-Asp-D-Val-Ala-D-Trp); cyclo(D-Asp-Ala-D-Val-Pro-D-Trp); cyclo(D-Asp-Pro-D-Val-Ile-D-Trp); cyclo(D-Asp-Pro-D-Val-Nlle-D-Trp); cyclo(D-Cys($O_3$Na)-Cys($O_3$Na)-D-Val-Leu-D-Trp); cyclo(D-CYs($O_3$Na)-Pro-D-Alle-Leu-D-Trp); cyclo(D-Asp-Val-D-Val-Leu-D-Trp); cyclo(D-Asp-Pro-D-Val-Nva-D-Trp); cyclo(D-Asp-Nlle-D-Val-Leu-D-Trp); cyclo(D-Asp-Pip-D-Val-Leu-D-Trp); cyclo(D-Asp-Phe-D-Val-Leu-D-Trp); cyclo(D-Cys($O_3$Na)-Glu-D-Val-Leu-D-Trp); cyclo(D-Cys($O_3$Na)-Lys-D-Val-Leu-D-Trp); cyclo(D-Asp-Pro-D-Val-Leu-D-Trp

22

(CHO)); cyclo(D-Glu-Ala-D-Alle-Leu-D-Trp(CHO)); cyclo(D-Asp-Pro-D-Alle-Leu-D-Trp(CHO)); cyclo(D-Asp-Ser-D-Val-Nle-D-Trp(CHO)); cyclo(D-Asp-Met-D-Val-Leu-D-Trp(CHO)); cyclo(D-Asp-Pro-D-Val-Nva-D-Trp(CHO)); cyclo(D-Asp-Lys(CHO)-D-Val-Leu-D-Trp(CHO)); cyclo(D-Asp-Met(O)-D-Val-Leu-D-Trp(CHO)); cyclo(D-Asp(ONa)-Pro-DVal-Leu-D-Trp); cyclo(D-Asp-Pro-D-Pen-Leu-D-Trp); cyclo(D-Asp-Aib-D-Val-Leu-D-Trp); cyclo(D-Asp-Pro-Aib-Leu-D-Trp); cyclo(D-Asp-Pro-$AC_5$C-Leu-D-Trp); cyclo(D-Asp-Pro-$AC_6$C-Leu-D-Trp); cyclo(D-Asp-Sar-D-Val-Leu-D-Trp); cyclo(D-Asp-β-Ala-D-Val-Leu-D-Trp); cyclo(D-Asp-Pro-D-Thg-Leu-D-Trp); cyclo(D-Asp-Thz-D-Val-Leu-D-Trp); cyclo(D-Asp-Pro-D-Val-MeLeu-D-Trp); cyclo(D-Asp-MeMet-D-Val-Leu-D-Trp); cyclo(D-Asp-Sar-D-Thg-Leu-D-Trp); cyclo(D-Asp-CpGly-D-Thg-Leu-D-Trp); cyclo(D-Asp-Pro-D-Dpg-Leu-D-Trp); cyclo(D-Cys($O_3$Na)-Pro-D-Thg-Leu-D-Trp(CHO)); cyclo(D-Cys($O_3$Na)-Pro-D-Thg-Leu-D-Trp); cyclo(D-Asp-Met($O_2$)-D-Val-Leu-D-Trp(CHO)); cyclo(D-Asp-PrGly-D-Thg-Leu-D-Trp); cyclo(D-Asp-trans-Hyp-D-Thg-Leu-D-Trp); cyclo(D-Asp-Pro-D-Fug-Leu-D-Trp); cyclo(D-Asp-Pro-D-Cpg-Leu-D-Trp); cyclo(D-Asp-Pro-D-Etg-Leu-D-Trp); cyclo(D-Asp-CmGly-D-Thg-Leu-DoTrp); cyclo(D-Asp-Pro-D-Val-His-D-Trp); cyclo(D-Asp-IeGly-D-Val-Leu-D-Trp); cyclo(D-Asp-Pro-D-Val-Leu-D-Trp(COO$CH_3$)); cyclo(D-Asp-Pro-D-Val-Leu-D-Trp(COO$^t$Bu)); cyclo(D-Asp-Pro-D-Val-Leu-D-Trp (O)); cyclo(D-Asp-MeAla-D-Val-Leu-D-Trp(O)); cyclo(D-Asp-Pro-D-Val-Leu-D-Trp($CH_2$OO$CH_3$)); cyclo(D-Asp-Pro-D-Val-Leu-D-Trp($CH_2$CON$H_2$)); cyclo(D-Asp-Pro-D-Val-Leu-D-Trp($CH_2$CONH$CH_3$)); cyclo(D-Glu-Ala-D-Val-Leu-D-Nal); cyclo(D-Asp-trans-Hyp-D-Cpg-Leu-D-Trp); cyclo(D-Asp-Pro-D-Val-Leu-D-Trp($CH_2$COOH)); cyclo(D-Asp-Ala-D-Val-$C_6$al-D-Trp); cyclo(D-Asp-Pro-D-Val-Leu-D-Phe); or cyclo(D-Asp-Pro-D-Val-Leu-D-Tyr).

Preferred cyclic peptides include cyclic pentapeptides and cyclic hexapeptides of formula (I) in which $X^1$ is D-Tyr or D-Asp; $X^2$ is Phe, Ala, $Ac_3c$ or Pro; $X^3$ is D-His, D-Ala, D-Val, Gly or β-Ala; and $X^4$ is D-His, L-His Ala, β-Ala, Aib, Gly, D-His-gly or Leu, provided that $X^1$, $X^2$, $X^3$ and $X^4$ are not selected such that the peptide of formula (I) is cyclo(D-Asp-Pro-D-Val-Leu-D-Trp), cyclo(D-Asp-Ala-D-Val-Leu-D-Trp), cyclo(D-Asp-Phe-D-Val-Leu-D-Trp), or cyclo(D-Asp-Pro-D-Val-His-D-Trp).

More preferred compounds of formula (I) include: cyclo(D-Tyr-Phe-D-His-Gly-D-Trp); cyclo(D-Tyr-Phe-D-His-β-Ala-D-Trp); cyclo(D-Tyr-Ala-D-Ala-Ala-D-Trp); cyclo(D-Asp-Ala-D-His-Ala-D-Trp); cyclo(D-Asp-Ala-D-Val-Aib-D-Trp); cyclo(D-Asp-Pro-D-Ala-Aib-D-Trp); cyclo(D-Asp-Ala-D-His-Leu-D-Trp); and cyclo(D-Tyr-Phe-Gly-D-His-Gly-D-Trp); cyclo(D-Tyr-$Ac_3c$-D-Val-Leu-D-Trp) and cyclo(D-Asp-$Ac_3c$-D-Val-Leu-D-Trp).

Most preferred peptides of the above include: cyclo(D-Tyr-Ala-D-Ala-Ala-D-Trp) and cyclo(D-Tyr-Phe-D-His-β-Ala-D-Trp). Cyclo(D-Asp-$Ac_3c$-D-Val-Leu-D-Trp) is also preferred, particularly because it also exhibits substantial affinity for $ET_B$ receptors.

Cyclic pentapeptides and cyclic hexapeptides of formula (II) are also provided:

$X^1$-L-Phe-$X^3$-$X^4$-$X^5$  (II)

in which $X^1$ is D-Tyr, D-Asp or D-Glu, $X^3$ is D-His, β-Ala-D-His, or gly-D-His; $X^4$ is Gly, D-His or β-Ala and $X^5$ is D-Trp or N-Me-D-Trp.

Preferred peptides of formula (II) include: cyclo(X-L-Phe-His-Gly-D-Trp); cyclo(X-L-Phe-D-His-β-Ala-D-Trp); cyclo(X-L-Phe-D-His-Gly-N-Me-D-Trp); cyclo(D-Tyr-Phe-β-Ala-D-His-D-Trp); cyclo(X-L-Phe-β-Ala-D-His-Gly-D-Trp); cyclo(X-L-Phe-Gly-D-His-Gly-D-Trp); and cyclo(D-Asp-Ala-D-Val-Aib-α-Me-D-Trp) in which X is D-Tyr, D-Asp or D-Glu.

(b) L-Trp-containing cyclic peptides

Also provided are substantially pure cyclic peptides, or pharmaceutically acceptable salts thereof, that contain between 5 and 7 residues that match the surface features of the C-terminal portion of endothelin-1 and that contain an L-Trp. These peptides includes cyclic peptides of the formula structure $D-X^1-D-X^2-L-X^3-D-X^4-L-Trp$ or $D-X^1-L-X^2-D-X^3-L-X^4-L-Trp$, in which D and L designate the stereoisomer of each amino acid residue and the superscripts are as defined above;

the C-terminal portion of endothelin-1 encompasses residues 13–21 that have the coordinates set forth in FIG. 1;

the coordinates of the cyclic peptide matches the coordinates of the C-terminal portion of endothelin-1;

the match is a goodness of fit of between about 60% and about 100% as defined by Equation (1):

$$G = 100(1 - X/n); \quad (1)$$

$$X = \sum_{i=1}^{n} ((r(a) - r(b)) \times (r(a) - r(b)))_i$$

for i=1-n in which n is 9 and r(a) and r(b) are the coordinates of ith atom of molecule (a) and (b), respectively; molecule (a) is the C-terminal portion of endothelin-1.

Among these peptides are cyclic peptides of formula (III):

$$cyclo(X^1-X^2-X^3-X^4-L-Trp) \quad (III)$$

and pharmaceutically acceptable salts and esters and other derivatives thereof in which $X^1$ is D-Ala, Aib, Gly, D-Val, D-Leu, D-Ile, D-Nva, D-Nle, or D-Alle; $X^2$ is D-Val, D-Leu, D-Ile, D-Ala, D-Gln, Gly, Aib, D-Nva, D-Nle, and D-Alle; $X^3$ is L-Pro, Gly, Aib, L-Val, L-Leu, L-Nva, L-Nle, L-Alle, or L-Hyp and $X^4$ is D-Asp, D-Glu, D-Ser, D-Thr, D-Tyr, D-Cys($O_3H$), or D-Pen($O_3H$).

Among the preferred peptides of formula (III) and pharmaceutically acceptable salts and esters thereof are those in which $X^1$ is D-Ala, D-Leu, Aib, or Gly; $X^2$ is D-Val, D-Leu, D-Ile, D-Ala or D-Gln; $X^3$ is L-Pro; and $X^4$ is D-Asp, D-Glu, or D-Ser. When $X^2$ is D-Gln, the peptides of formula (III) should preferentially bind to $ET_B$ receptors.

In particular, the following peptides of formula (III) are preferred: cyclo(D-Leu-D-Val-L-Pro-D-Asp-L-Trp); D-Leu-D-Val-L-Pro-D-Glu-L-Trp; cyclo(D-Ala-D-Val-L-Pro-D-Asp-L-Trp); cyclo(D-Ala-D-Val-L-Pro-D-Glu-L-Trp); cyclo(D-Ala-D-Val-L-Pro-D-Ser-L-Trp); cyclo(D-Ala-D-Gln-L-Pro-D-Asp-L-Trp); cyclo(D-Ala-D-Gln-L-Pro-D-Glu-L-Trp-D-Ala-D-Gln); cyclo(D-Ala-D-Gln-L-Pro-D-Ser-L-Trp); cyclo(Gly-D-Val-L-Pro-D-Asp-L-Trp); cyclo(Gly-D-Val-L-Pro-D-Glu-L-Trp); cyclo(Gly-D-Val-L-Pro-D-Ser-L-Trp); cyclo(Gly-D-Gln-L-Pro-D-Asp-L-Trp); cyclo(Gly-D-Gln-L-Pro-D-Glu-L-Trp); cyclo(Gly-D-Gln-L-Pro-D-Ser-L-Trp); cyclo(Aib-D-Gln-L-Pro-D-Asp-L-Trp); cyclo(Aib-D-Gln-L-Pro-D-Glu-L-Trp); cyclo(Aib-D-Gln-L-Pro-D-Ser-L-Trp); cyclo(Aib-D-Gln-L-Pro-D-Asp-L-Trp); cyclo(Aib-D-Gln-L-Pro-D-Glu-L-Trp); and cyclo(Aib-D-Gln-L-Pro-D-Ser-L-Trp).

Cyclic peptides having formula (IV):

$$X^1-X^2-X_3-X^4-L-Trp \quad (IV)$$

and pharmaceutically acceptable salts and esters and other pharmaceutically acceptable derivatives thereof in which $X^1$ is D-Leu, D-Val, D-Ile, D-Ala, Gly, Aib, D-Nva, D-Nle or D-Alla; $X^2$ is Val, Ile, Leu, Ale, Gln, Gly, Aib, L-Nva, L-Nle or L-Alla; $X^3$ is D-Pro, D-Hyp, D-Ala, D-Val, D-Ile, Gly, Aib, D-Nva, D-Nle or D-Alla; and $X^4$ is L-Asp, L-Glu, L-Tyr, L-Ser, L-Thr, L-Cys($O_3H$), or L-Pen ($O_3H$) are provided.

Among the preferred peptides of formula (IV) and pharmaceutically acceptable salts and esters thereof are those in which $X^1$ is D-Leu, D-Val, D-Ile, or D-Ala; $X^2$ is L-Val, L-Ile, L-Leu or L-Ala; $X^3$ is D-Pro, D-Ala, D-Val or D-Ile; and $X^4$ is L-Asp, L-Glu, L-Tyr or L-Ser. Peptides of formulas: cyclo(D-Leu-L-Val-D-Pro-L-Asp-L-Trp); cyclo(D-Leu-L-Val-D-Pro-L-Tyr-L-Trp); cyclo(D-Leu-L-Val-D-Pro-L-Ser-L-Trp); cyclo(D-Leu-L-Val-D-Pro-L-Glu-L-Trp); and cyclo(D-Leu-L-Val-D-Ala-L-Asp-L-Trp) are among the more preferred peptides of formula (IV).

More preferred cyclic peptides are any of the cyclic peptides that inhibit binding of endothelin-1 to $ET_A$ receptors or $ET_B$ receptors at an $IC_{50}$ of less than or equal to about 150 μM, and preferably less than 100 μM and more preferably, less than about 50 μM. Such cyclic peptides include, but are not limited to: cyclo(D-Tyr-Phe-His-β-Ala-D-Trp), cyclo(D-Leu-L-Val-D-Pro-L-Asp-L-Trp) and cyclo (D-Leu-L-Val-D-Pro-L-Asp-L-Trp).

(2) Synthesis of the cyclic peptides that mimic surface features of endothelin

The cyclic peptide endothelin-1 surface feature mimics may be synthesized by any method for synthesis of cyclic peptides known to those of skill in the art. Such methods for peptide synthesis are known in the art. Some of the cyclic peptide endothelin-1 surface feature mimics have been synthesized as described in the Examples by solid phase peptide synthesis on 1% crosslinked polystyrene with an oxime resin (see, De Grado et al. (1980) *J. Org. Chem.* 45: 1295–1300). The peptides were synthesized using the Boc synthesis strategy with benzyl (Bzl) type side chain protection. Activation of the amino acid derivatives was accomplished with diisopropylcarbodiimide (DIC).

Cleavage of the synthesized peptide from the resin and cyclization was effected in one step (see, Osapay et al. (1991) *Techniques in Protein Chemistry* 2:2–11; Osapay et al. (1990) *Tetrahedron Lttr.* 43: 6121–6124; and Osapay et al. (1990) *J. Amer. Chem. Soc.* 112: 6046–6051) in which cleavage is initiated by the free N-terminal amino group, which attacks the C-terminal carboxy group on the oxime linker. The reaction was carried out in about ten-fold excess acetic acid, which catalyzes the cyclization reaction. In instances in which solubility in the reaction mixture was low, cleavage was effected in DCM or DCM/DMF. In order to favor intrachain reaction over interchain reaction, the substitution level on the resin was low, about 0.2 mmol/g. This was accomplished by substituting the resin with fewer amino acid groups than oxime groups. Free oxime groups were capped using trimethyl acetic anhydride, which was more effective for capping than normal acetic anhydride. Side chains of the of the crude peptides were cleaved either by catalytic hydrogenation in 10% acetic acid in methanol resuspended in TFE/HFIP or by HF with thioanisole/indole. Trp was deprotected using 20% piperidine in DM.

Crude aleprotected cyclic peptides were purified by HPLC using a Waters (Bedford, Mass.) cartridge system (25 mm×10 cm/hr) with Novapak™ $C_{18}$ packing and a gradient composed of 0.1% TFA/water and 0.1% TFA/CH$_3$CN. The final products were lyophilized and analyzed by HPLC, FAB-MS and amino acid analysis.

(C) Evaluation of the bioactivity of the cyclic peptides

After synthesis the bioactivity of the cyclic peptides may be evaluated. Standard physiological, pharmacological and biochemical procedures are available for testing the cyclic peptide endothelin-1 surface feature mimics to identify the peptides that possess any biological activities of an endothelin peptide or the ability to interfere with or inhibit endothelin peptides.

(1) Screening Compounds for the Ability to Modulate the Activity of an Endothelin Peptide After synthesis, the cyclic peptides may be tested for the ability to modulate the activity of endothelin-1. Standard physiological, pharmacological and biochemical procedures are available for testing the compounds to identify those that possess any biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors, and are candidates for use in the methods of treating endothelin-mediated disorders.

Numerous assays are known to those of skill in the art for evaluating the ability of compounds to modulate the activity of endothelin (see, e.g., EP 0436189 A1 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177: 171–176). In vitro studies may be corroborated with in vivo studies (see, e.g., EP 0436189 A1 to BANYU PHARMACEUTICAL CO., LTD. (Oct. 7, 1991)) and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., Tissue selectivity of endothelin, *Eur. J. Pharmacol* 165:223–230, (1989)). The ability to act as an endothelin antagonist in vivo can be tested in hypertensive rats, spontaneously hypertensive rats, ddy mice or other recognized animal models (see, Kaltenbronn et al. (1990) *J. Med. Chem.* 33:838–845, see, also, U.S. Pat. No. 5,114,918 to Ishikawa et al.; and EP A10 436 189 to BANYU PHARMACEUTICAL CO., LTD (Oct. 7, 1991); see, also Bolger et al. (1983) *J. Pharmacol. Exp. Ther.* 225291–309; Stein et al. (1994) *J. Med. Chem.* 37:329–331; and Clozel et al. (1993) *Nature* 365:759–761). Using the results of such animal studies, pharmaceutical effectiveness may be evaluated and pharmaceutically effective dosages determined. A potential agonist may also be evaluated using in vitro and in vivo assays known to those of skill in the art.

Endothelin activity can be identified by the ability of a test compound to stimulate constriction of isolated rat thoracic aorta (Borges et al. (1989) "Tissue selectivity of endothelin" *Eur. J. Pharmacol.* 165: 223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi et al. (1991) *Reg. Pep.* 32: 23–37, Panek et al. (1992) *Biochem. Biophys. Res. Commun.* 183: 566–571). For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797), $ET_A$ receptors are not detected in cultured endothelial cells, which express $ET_B$ receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Filep et al. (1991) *Biochem. and Biophys Res. Commun.* 177: 171–176). Thus, the relative affinity of the cyclic peptides for different endothelin receptors may be evaluated by determining the inhibitory dose response curves using tissues that differ in receptor subtype. A potential agonist may also be evaluated using in vitro and in vivo assays known to those of skill in the art.

Using such assays, the relative affinities of the cyclic peptides for $ET_A$ receptors and $ET_B$ receptors have been and can be assessed. Those that possess the desired properties, such as specific inhibition of binding of endothelin-1, are selected. The selected cyclic peptides that exhibit desirable activities may be therapeutically useful and are tested for such use using the above-described assays from which in vivo effectiveness may be evaluated (see, e.g., U.S. Pat. No. 5,248,807; U.S. Pat. No. 5,240,910; U.S. Pat. No. 5,198,548; U.S. Pat. No. 5,187,195; U.S. Pat. No. 5,082,838; U.S. Pat. No. 5,230,999; published Canadian Application Nos. 2,067, 288 and 2,071,193; published Great Britain Application No. 2,259,450; Published International PCT Application No. WO 93/08799; Benigi et al. (1993) *Kidney International* 44:440–444; Nirei et al. (1993) *Life Sciences* 52:1869–1874; Stein et al. (1994) *J. Med. Chem.* 37:329–331; and Clozel et al. (1993) *Nature* 365:759–761). Cyclic peptides that exhibit activities that correlate with in vivo effectiveness will then be formulated in suitable pharmaceutical compositions and used as peptidomimetics without further modification.

The cyclic peptides also may be used in methods for identifying and isolating endothelin-specific receptors and as models for the design of peptidomimetics.

(2) Affinity Isolation of Endothelin Receptors

A method for identifying endothelin receptors is provided. In practicing this method, one or more of the cyclic peptides is linked to a support and used in methods of affinity purification of receptors. By selecting the cyclic peptides with particular specificities, distinct subclasses of ET receptors may be identified.

One or more of the cyclic peptides may be linked to an appropriate resin, such as Affi-gel, covalently or by other linkage, by methods known to those of skill in the art for linking endothelin to such resins (see, Schvartz et al. (1990) *Endocrinology* 126: 3218–3222). The linked peptides can be those that are specific for $ET_A$ or $ET_B$ receptors or other subclass of receptors. For example, peptides of the formula cyclo($X^1$-$X^2$-L-Pro-$X^4$-L-Trp) in which $X^1$ is D-Ala, Aib, or Gly, $X^4$ is D-Asp, D-Glu, or D-Ser, and $X^2$ is D-Gln should be $ET_B$ specific and may be used for identification of receptors that have binding properties similar to $ET_B$ receptors.

The resin is pre-equilibrated with a suitable buffer generally at a physiological pH (7 to 8). A composition containing solubilized receptors from a selected tissue are mixed with the resin to which the cyclic peptide is linked and the receptors are selectively eluted. The receptors can be identified and further characterized by testing them for binding to an endothelin isopeptide or analog or by other methods by which proteins are identified and characterized. Preparation of the receptors, the resin and the elution method may be performed by modification of standard protocols known to those of skill in the art (see, e.g., Schvartz et al. (1990) *Endocrinolofiy* 126:3218–3222).

A method for distinguishing specificities among endothelin receptors is also provided. Any of the assays described herein, or others known to those of skill in this art, for measuring the affinity of selected compounds for endothelin receptors may also be used to distinguish receptors subtypes based on affinity for particular cyclic peptides provided herein. Thus, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

In particular, $ET_A$ and $ET_B$ receptors or receptors sharing certain affinities with either receptor may be identified by comparing the binding affinity of each receptor for the peptides of formula cyclo($X^1$-$X^2$-L-Pro-$X^4$-L-Trp) in which $X^1$ is D-Ala, Aib, or Gly; $X^4$ is D-Asp, D-Glu, or D-Ser, and $X^2$ is D-Gln with the binding of such peptides affinity of such receptors for peptides in which $X^2$ is D-Val, D-Leu, D-Ile or D-Ala. Peptides in which $X^2$ is D-Val, D-Leu, D-Ile or D-Ala should preferentially interact with $ET_A$ receptors compared to $ET_B$ receptors. Peptides in which $X^2$ is Gln should preferentially interact with $ET_B$ receptors.

Selected receptors may then be used in drug screening assays to identify compounds that specifically bind to these receptors.

Thus, by selecting or designing cyclic peptide endothelin analogs or peptidomimetics that mimic particular surface features of an endothelin isopeptide, new subclasses of endothelin receptors may be identified. Such information may then be used in the design of disease-specific analogs and peptidomimetics.

Design of Suitable Peptidomimetics Based on the Conformation of the Cyclic Peptides and Analysis of the Biological Activity of the Peptidomimetics Additional peptidomimetic compounds, based on the structure and activity of previously evaluated cyclic peptides or chemically modified analog(s) thereof may be designed by replacing residues of the cyclic peptides or endothelin analogs with residues that are bioisosteric with respect to the replaced residues. For example, by reference to available data bases, such as the Cambridge crystallographic data base, replacement residues which are bioisosteric with various residues of the compound of interest can be identified and used to replace the native residue in the compound of interest. Those of skill in the art can identify suitable bioisosteric moieties which can be used in place of the naturally occurring amino acid residues. Examples of some commonly used bioisosteric moieties have been presented in copending U.S. application Ser. No. 08/223,513 and U.S. Pat. No. 5,331,573.

Identification of any flexible portions of the structure that should be replaced with suitable rigid or conformationally constrained bioisostere(s) is an important consideration in designing the peptidomimetic. Any portions or sections of the structure subject to degradation when the analog is administered may also be replaced with bioisosteres or equivalents that are not readily biologically degraded, and that maintain the desired binding between target peptides and receptors or peptidomimetics. Selected replacements will depend upon the mode of administration, which includes, oral administration, inhalation, topical application, intramuscular injection, intravenous injection, subcutaneous injection and other modes of administration known to those of skill in this art. Oral administration and parenteral administration are preferred herein.

In addition, various substituents on the amide nitrogen and the α-carbon can be bound to one another to form cyclic structures to produce a constrained analog. Other constrained, cyclic structures may also be produced by linking other substituents. Since the replacement residues and the bonds in the constrained cyclic structures should not be recognized by the enzymes that degrade naturally occurring proteins, the chemically modified analogs typically are much more resistant to enzymatic cleavage than are the unmodified peptides from which they are derived. In addition, the wide range of possible replacement groups which can be used to modify the backbone and side chains of peptides affords the opportunity to reduce the conformational flexibility of the parent structure. Thus, the possibility that the peptide will adopt conformation(s) other than the specifically desired conformation(s) can be substantially minimized by appropriate modification of the peptide.

Once the desired analog, including backbone and side chain modification, as appropriate, has been identified, chemical synthesis using standard synthetic techniques will be undertaken. For a given analog, the skilled artisan can identify suitable synthetic approaches for the preparation of the peptidomimetic.

Formulation of Pharmaceutical Compositions

Effective concentrations of one or more of the cyclic peptides of formulas (I)–(IV) or pharmaceutically acceptable salts, esters or other derivatives thereof are mixed with a suitable pharmaceutical carrier or vehicle. The concentrations of the cyclic peptides are effective for delivery of an amount, upon administration, that ameliorates the symptoms of the endothelin-mediated disease. Typically, the compositions are formulated for single dosage administration.

Upon mixing or addition of the cyclic peptide(s), the resulting mixture may be a solution, suspension, emulsion or the like. The form of the resulting mixture depends upon a number of factors, including the intended mode of administration and the solubility of the peptide in the selected carrier or vehicle. The effective concentration is sufficient for ameliorating the symptoms of the disease, disorder or condition treated and may be empirically determined.

Pharmaceutical carriers or vehicles suitable for administration of the cyclic peptides provided herein include any such carriers known to those skilled in the art to be suitable for the particular mode of administration. In addition, the cyclic peptides may be formulated as the sole pharmaceutically active ingredient in the composition or may be combined with other active ingredients.

The active cyclic peptides can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration. The active cyclic peptide is included in the pharmaceutically acceptable carrier in an amount sufficient to exert a therapeutically useful effect in the absence of undesirable side effects on the patient treated.

The therapeutically effective concentration may be determined empirically by testing the cyclic peptides in known in vitro and in vivo systems (see, e.g., U.S. Pat. No. 5,114,918 to Ishikawa et al.; EP A1 0 436 189 to BANYU PHARMACEUTICAL CO., LTD (Oct. 7, 1991); Borges et al. (1989) *Eur. J. Pharm.* 165: 223–230; : Filep et al. (1991) *Biochem. Biophys. Res. Commun.* 177: 171–176) and then extrapolating therefrom for dosages for humans.

The concentration of active cyclic peptide in the drug composition will depend on absorption, inactivation and excretion rates of the active cyclic peptide, the dosage schedule, and amount administered as well as other factors known to those of skill in the art.

Pharmaceutical carriers or vehicles suitable for administration of the cyclic peptides provided herein include any such carriers known to those skilled in the art to be suitable for the particular mode of administration. In addition, the cyclic peptides may be formulated as the sole pharmaceutically active ingredient in the composition or may be combined with other active ingredients.

The active cyclic peptides can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

Typically a therapeutically effective dosage should produce a serum concentration of active ingredient of from about 0.1 ng/ml to about 50–100 µg/ml/kg body weight. The pharmaceutical compositions typically should provide a dosage of from about 0.01 mg to about 2000 mg of cyclic peptide per kilogram of body weight per day. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the cyclic peptide should be provided in a composition that protects it from the acidic environment of the stomach. For example, the composition can be formulated in an enteric coating that maintains its integrity in the stomach and releases the active cyclic peptide in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active cyclic peptide or cyclic peptides can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or cyclic peptides of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The cyclic peptides can also be administered as a component of an elixir, suspension, syrup, wafer, chewing gum or the like. A syrup may contain, in addition to the active cyclic peptides, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the cyclic peptide is used for treating asthma or hypertension, with other bronchodilators and antihypertensive agents, respectively.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active cyclic peptides may be prepared with carriers that protect the cyclic peptide against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The cyclic peptides may be formulated for local or topical application, such as for topical application to the skin in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The cyclic peptides may be formulated as aerosols for topical application, such as by inhalation (see, e.g., U.S. Pat. Nos. 4,044,126, 4,414,209, and 4,364,923, which describe aerosols for delivery of asteroid useful for treatment inflammatory diseases, particularly asthma).

Finally, the cyclic peptides may be packaged as articles of manufacture containing packaging material, a cyclic peptide provided herein, which is effective for antagonizing the effects of endothelin, ameliorating the symptoms of an endothelin-mediated disorder, or inhibiting binding of an endothelin peptide to an ET receptor with an $IC_{50}$ of less than about 100 μM, within the packaging material, and a label that indicates that the cyclic peptide or salt thereof is used for antagonizing the effects of endothelin, treating endothelin-mediated disorders or inhibiting the binding of an endothelin peptide to an ET receptor.

The following examples are included for illustrative purposes only and are not intended to limit the scope of the invention.

EXAMPLES

Synthesis of Endothelin Analogs

The following endothelin analogs were synthesized:

(1): cyclo(D-Tyr-Phe-DoHis-Gly-D-Trp);

(2): cyclo(D-Tyr-Phe-D-His-β-Ala-D-Trp);

(3): cyclo(D-Glu-Ala-D-Val-Leu-DoTrp);

(4): cyclo(D-Tyr-Phe-Gly-D-His-Gly-D-Trp);

(5): cyclo(D-Asp-Pro-D-Val-Leu-D-Trp);

(6): cyclo(D-Asp-Ala-D-Ala-Ala-D-Trp);

(7): cyclo(D-Tyr-Ala-D-Ala-Ala-D-Trp); and (8): cyclo(D-Leu-Val-D-Pro-Asp-Trp)

(9) cyclo(D-Asp-Ac$_3$c-D-Val-Leu-D-Trp).

Compounds (3) and (5), which have activity as endothelin antagonists, were synthesized for use as controls (see, EP 0436189 A1 to BANYU PHARMACEUTICAL CO., LTD. (Oct. 7, 1991)).

Example 1

Synthesis of cyclo(D-Tyr-Phe-D-His-Gly-D-Trp) (1)

A. Preparation of Boc-D-Trp(For)-oxime resin.

One percent crosslinked polystyrene substituted with the oxime linker (2.01 g) was preswollen in 30 ml DCM for 30 min in a 60 ml reaction vessel. Boc-D-Trp(For)-OH (0.13 g, 0.4 mmol) and DCC (0.082 g, 0.4 mmol) was dissolved in 10 ml DCM and stirred for 30 min at room temperature. The solution was removed and the resin was washed as follows: 2×10 ml DMF/DCM (1:1), 2×10 ml DCM, 2×10 ml ethanol/DCM (1:1), and 2×10 ml DCM. The remaining free oxime groups were capped with 3.0 ml (14.8 mmol) trimethyl acetic anhydride and 1.0 ml (5.74 mmol) DIEA in 11 ml DCM at room temperature overnight, after which the resin was washed with 4×20 ml DCM, 2×20 ml ethanol and then dried. The yield was 2.17 g.

Substitution was determined using the picric acid test (Steward et al. (1984) in *Solid Phase Peptide Synthesis*, Freeman, W. H., Pierce, N.Y., pages 105–122). The test was performed in triplicate in three separate glass filter funnels. About 20 mg of resin was introduced into each glass filter funnel and washed with 2×1 ml DCM, followed by 1 min cleavage with 1 ml 25% TFA in DCM and 20 min cleavage with 1 ml 25% TFA in DCM. The filter was washed with 2×1 ml DCM, neutralized with 1 ml 5% DIEA in DCM, washed with 2×1 ml DCM, neutralized with 1 ml 5% DIEA in DCM, and washed with 3×1 ml DCM. Picric acid (3×1 ml 0.1M (2.29 g/100 ml) DCM was adsorbed to the material in the filter funnels, washed with 6×1 ml DCM, desorbed with 3×1 ml 5% DIEA, and the resulting solution was collected. The material in the funnels was washed with 3×1 ml DCM and the filtrate combined with the collected solution. The resulting solution was diluted to 100 ml with 95% ethanol and the absorbance(OD) at 358 nm ($\epsilon$=14,500) was measured.

The amount of substitution (nmol/g)=(OD×volume (ml)) /($\epsilon$×weight (g))=0.1195 nmol/g for the Boc-D-Trp(for)-oxime resin.

B. Preparation of D-Tyr(BrZ)-Phe-D-His(Bom)-Gly-D-Trp(For) oxime resin.

The D-Trp(For)-oxime resin was washed with 2×10 ml DCM, followed by 1 min cleavage with 1×10 ml 25% TFA in DCM and 30 min cleavage with 1×10 ml 25% TFA in DCM. The resulting material was washed with 2×10 ml DCM, 1×10 ml isopropanol, 2×10 ml DCM, 1×10 ml isopropanol, 2×10 ml DCM, neutralized with 3×10 ml 5% DIEA in DCM, and washed with 4×10 ml DCM. The material was then coupled for 60 min with 3 eq Boc-aa-OH, in which aa is the next amino acid in the chain. In this instance, Gly. Prior to coupling, the Boc-aa-OH had been preactivated by treatment for 30 min with 3 eq DIC in 10 ml DCM. The resin was washed with 2×10 ml DMF/DCM (1:1), 2×10 ml DCM, 2×10 ml ethanol/DCM (1:1), and 2×10 ml DCM. About 5 mg of the resin was collected for a ninhydrin test. The remainder was acetylated for 60 min with 3 eq trimethylacetic anhydride/2.2 eq DIEA in 10 ml DCM and washed with 4×10 ml DCM.

To couple the third residue, D-His in this instance, the above procedure was repeated, except that the last neutralization step and subsequent washings were eliminated. Five eq, rather than 3 eq, of protected and activated amino acid were added to the resin. The base (1.2 eq DIEA) was added to the resin after the protected and activated amino acid was added. No HOBt was added. The last two amino acid residues, L-Phe and D-Tyr in this instance, were sequentially coupled to the peptide, with appropriate protecting groups, where necessary, using the above procedure.

C. Cyclization of the Peptide on Oxime Resin.

The product of step B (1.1 g, 0.132 mmol) was placed in a solid phase reaction vessel with 15 ml DCM for 30 min. The Boc group was cleaved as described in the synthesis protocol (Example 1.B.) after which 68 μl (0.12 mmol) of acetic acid in 15 ml DCM was added to the resin and the resulting mixture was shaken at room temperature for 15 hours.

The solution was then filtered and collected. The resin was washed with 4×10 ml DCM, 2×10 ml DCM, 2×10 ml isopropanol and 2×10 ml DCM. The filtrate and washes were combined and evaporated. The concentrate was added dropwise to 50 ml dry and cold ether. The colorless precipitate was collected by centrifugation, the solution decanted and the residue washed with 2×30 ml ether. The crude peptide was then purified by HPLC using a gradient composed of 0.1% TFA in water and 0.1% TFA in CH$_3$CN.

D. Removal of side chain protective groups

To cleave the formyl group from Trp, the crude cyclic peptide was stirred in 20% piperidine in DMF at room temperature for 1 hr. The solvent was evaporated and the residue was dried. The Tyr, Asp and His side chain protective groups, Brz, Bzl, and Bom, respectively, were removed by catalytic hydrogenation.

Catalytic hydrogenation was typically accomplished by dissolving the peptide in 3 ml HFIP and diluting with 3 ml TFE. Pd/C catalyst was added and the mixture was hydrogenolyzed at room temperature for 15 hours. The catalyst was removed by filtration over celite and washed with 3×1 ml TFE and 5×2 ml methanol. The solution was concentrated to about 1 ml and added dropwise to 35 ml ice cold dry ether. The precipitated peptide was collected by centrifugation, the solution decanted and the residue was washed with 2×30 ml ether. The product was dried, diluted with 1 ml HFIP and water and then lyophilized. The final product, cyclo(D-Tyr-Phe-D-His-Gly-D-Trp) was purified by HPLC as described in step C above. For a typical procedure, the overall yield was 2.3%.

FAB-MS: m/z 691 (Theoretical m/z: 690.79) Amino acid analysis: Tyr (1.08), Phe (0.99), His (1.00), Gly (0.92) Trp not determined.

Example 2

Synthesis of cyclo(D-Tyr-Phe-D-His-β-Ala-D-Trp) (2)

Using the method described in Example 1, cyclo(D-Tyr-Phe-D-His-β-Ala-D-Trp) was prepared.

FAB-MS: m/z 705 (Theoretical m/z: 704.81) Amino acid analysis: Tyr (0.96), Phe (0.99), His (1.05), Trp and β-Ala not determined.

Example 3

Synthesis of cyclo(D-Glu-Ala-D-Val-Leu-D-Trp) (3)

Using the method described in Example 1, cyclo(D-Glu-Ala-D-Val-Leu-D-Trp) was synthesized.

FAB-MS: m/z 599 (Theoretical m/z: 598.72) Amino acid analysis: Glu (1.02), Ala (1.01), Val (0.95), Leu (1.01), Trp not determined.

Example 4

Synthesis of Cyclo(D-Tyr-Phe-Gly-D-His-Gly-D-Trp) (4)

Using the method described in Example 1, cyclo(D-Tyr-Phe-Gly-D-His-Gly-D-Trp) was synthesized with a 1.5% overall yield.

FAB-MS: m/z 748 (Theoretical m/z: 747.85) Amino acid analysis: Tyr (1.02), Phe (1.05), Gly (1.76), His (1.18), Trp not determined.

Example 5

Synthesis of cyclo(D-Asp-Pro-D-Val-Leu-D-Trp) (5)

Using the method described in Example 1, cyclo(D-Asp-Pro-D-Val-Leu-D-Trp) was synthesized and resulted in a 15% overall yield.

FAB-MS: m/z 611 (Theoretical m/z: 610.74) Amino acid analysis: Asp (1.06), Pro (1.07), Val (0.91), Leu (0.97), Trp not determined.

Example 6

Synthesis of cyclo(D-Asp-Ala-D-Ala-Ala-D-Trp) (6)

Using the method described in Example 1, cyclo(D-Asp-Ala-D-Ala-Ala-D-Trp) was synthesized.

FAB-MS: m/z 515 (Theoretical m/z: 514.56) Amino acid analysis (1.01), Ala (2.99), Trp not determined.

Example 7

Synthesis of cyclo(D-Tyr-Als-D-Ala-Ala-D-Trp) (7)

Using the method described in Example 1, cyclo(D-TVr-Als-D-Ala-Ala-D-Trp) (7) was synthesized to produce a 5.5% overall Yield.

FAB-MS: m/z 563 (Theoretical m/z: 562.65) Amino acid analysis: Tyr (1.02), Ala (2.98), Trp not determined.

Example 8

Synthesis of cyclo(D-Leu-L-Val-D-Pro-L-Asp-L-Trp) (8)

A. Preparation of Boc-Trp-oxime resin

One percent crosslinked polystyrene substituted with the oxime linker (2.67 g=2.0 mmol) was preswollen in 60 ml DCM for 30 min. in a 60 ml reaction vessel. Boc-Trp-OH (1.216 g, 4.0 mmol) and DCC (0.825 g, 4.0 mmol) was dissolved in 60 ml DCM and stirred for about 15.5 hrs. at room temperature. The solution was removed and the resin was washed as follows: 2×40 ml DMF/DCM (1:1), 2×40 m DCM, 2×40 ml ethanol/DCM (1:1), and 2×40 ml DCM. The remaining free oxime groups were capped with 4.0 ml (19.71 mmol) trimethyl acetic anhydride and 1.3 ml (7.4 mmol) DIEA in 11 ml DCM at room temperature overnight, after which the resin was washed with 4×40 ml DCM, 2×25 ml ethanol and then dried. The yield was 3.3 g.

Substitution was determined using the picric acid test [Steward and Young (1984) in *Solid Phase Peptide Synthesis*, Freeman, W. H., Pierce, N.Y., pp. 105–122]. The test was performed in duplicate in three separate glass filter funnels. About 20 mg of resin (accurately weighed) was introduced into each glass filter funnel and washed with 2×1 ml DCM, followed by 1 min. cleavage with 1 ml 25% THF in DCM and 20 min. cleavage with 1 ml 25% TFA in DCM. The filter was washed with 2×1 ml DCM, neutralized with 1 ml 5% DIEA in DCM for 3 min., washed with 2×1 ml DCM, neutralized again with 1 ml 5% DIEA in DCM for 3 min., and washed with 3×1 ml DCM. Picric acid (3×1 ml 0.1M (2.29 g/100 mi DCM) was absorbed to the material in the filter funnels, washed with 6×1 ml DCM, desorbed with 3×1 ml. 5% DIEA, and the resulting solution was collected. The material in the funnels was washed with 3×1 ml DCM and the filtrate combined with the collected solution. The resulting solution was diluted to 100 ml with 95% ethanol and the absorbance(OD) at 358 nm ε=14,500) was measured.

The amount of substitution (nmol/g)=(OD×volume (ml)/ε×weight (g))=0.4075 nmol/g for the Boc-Trp-oxime resin.

B. Preparation of (D-Leu-Val-D-Pro-Asp-Trp) oxime resin.

The Trp-oxime resin (1 g, 0.406 mmol) was washed with 2×10 ml DCM, followed by 1 min cleavage with 1×10 ml 25% TFA in DCM. The resulting material was washed with 2×10 ml DCM, 1×10 ml isopropanol, 2×10 ml DCM, 1×10 ml isopropanol, 2×10 ml DCM, neutralized with 3×10 ml 5% DIEA in DCM, and washed with 4×10 ml DCM. The material was then coupled for 60 min. with 3 eq of Asp (OBzl) which was preactivated by treatment for 30 min. with 3 eq DIC in 10 ml DCM. The resin was washed with 2×10 ml DMF/DCM (1:1), 2×10 ml DCM, 2×10 ml ethanol/DCM (1:1), and 2×10 ml DCM. About 5 mg of the resin was collected for a ninhydrin test. The remainder was acylated for 60 min. with 3 eq trimethylacetic anhydride/2.2 eq DIEA in 10 ml DCM and washed with 4×10 ml DCM.

To couple the third residue, D-Pro, the above procedure was repeated, except that the neutralization step and subsequent washings were eliminated. Five eq, rather than 3 eq of preactivated protected amino acid were added to the resin. The base (1.2 eq DIEA) was added to the resin after the protected and activated amino acid were added. No HOBt was added. L-Val and D-Leu residues were sequentially coupled to the peptide using the above procedure.

C. Cyclization of the Peptide on Oxime Resin.

One half of the product of step B (0.631 g, 0.256 mmol) was placed in a solid phase reaction vessel with 20 ml DCM for 30 min. The Boc group was cleaved as described in Example 1.B after which 146.6 µl of acetic acid in 20 ml DCM was added to the resin and the resulting mixture was shaken at room temperature for 21 hrs.

The solution was then filtered and collected. The resin was washed 4×10 ml DCM, 2×10 ml DCM, 2×10 ml isopropanol and 2×10 ml DCM. The filtrate and washes were combined and evaporated. The crude peptide was then purified on silica gel column using 25:5 $CH_2Cl_2$/MeOH.

D. Removal of side chain protective groups

The side chain Bzl protective group on Asp was moved by catalytic hydrogenation. The peptide was dissolved in 3 ml MeOH. Pd/C catalyst was added and the mixture was hydrogenolyzed at room temperature for 2 hrs. The catalyst was removed by filtration, washed with 5×2 ml methanol. The solution was concentrated to dryness. The final product, cyclo(D-Leu-Val-D-Pro-Asp-Trp) was purified by HPLC as described in step C above and the overall yield was 24.1%.

Example 9

The synthetic peptides exhibited endothelin antagonistic activity

A. Assays

1. Endothelin Binding Inhibition Test #1 ($ET_A$ activity)

Ventricles from 4-day old rats were removed and rinsed in PBS. The tissue was minced with scissors, suspended in a solution of 0.1% collagenase in Dulbecco's Modified Eagles Medium (MEDIA) and incubated for 15 min at 37° C. in a shaking water bath. The tissue was then triturated, the dispersed cells removed and added to MEDIA containing 10% Fetal calf serum (HEART MEDIA). Fresh collagenase solution was added to the tissue and the above process was repeated three times. The dispersed cells were pooled, washed three times in heart media, placed in a T-75 tissue culture dish and incubated for one hour at 37° C. in an atmosphere of 5% $CO_2$. The flask was tapped gently several times and the media, containing mainly cardiocytes, removed and centrifuged at 30,000×g. The resulting pellet was resuspended in ultra pure water containing aprotinin (100 KIU/ml) and was homogenized using a Dounce homogenizer fitted with a loose fitting pestle. The cell/membrane suspension was frozen and thawed once and then recentrifuged at 30,000×g for 10 minute. The resultant membranes were resuspended in 30 mM HEPES buffer, pH 7.4, containing aprotinin (100 KIU/ml) to give a protein concentration of 5 mg/ml and stored at −70° C. until use.

Two µl of this membrane suspension were added to 98 µl of binding buffer (30 mM HEPES buffer, pH 7.4 containing 150 mM NaCl, 5 mM $MgCl_2$, 0.5% Bacitracin, 0.1% BSA). Fifty 50µl of (A) endothelin-1 (to measure non specific binding: to give a final concentration 80 nM), (B) binding buffer (to measure total binding), or (C) a test compound (final concentration 1 nM to 100 µM) was added to the membrane suspension. Each mixture was shaken and incubated at 25° C for 60 min. and 50 µl $^{125}$I-endothelin-1 (3,000 cpm) was added. Each mixture was shaken, incubated at 4° C. for 16 hours and centrifuged at 4° C. for 25 min at 2,500×g. The supernatant, containing unbound radioactivity, was decanted and the pellets counted on a Genesys multi-well gamma counter. The degree of inhibition of binding (D) was calculated according to the following equation:

$$\% D = 100 - \frac{(C)-(A)}{(B)-(A)} \times 100$$

Each test was performed in triplicate.

2. Endothelin Binding Inhibition Binding Test #2 ($ET_B$ activity)

COS-7 cells were transfected with DNA encoding the $ET_B$ receptor. Transfected cells that expressed the human $ET_B$ receptor were grown to confluence in T-175 flasks. Cells from multiple flasks were collected by scraping, pooled and centrifuged for 10 min. at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5 mM HEPES buffer, pH 7.4 containing aprotinin (100 KIU/ml)) and then frozen and thawed once. Five ml of buffer B (5 mM HEPES Buffer, pH 7.4 containing 10 mM $MnCl_2$ and 0.001% deoxyribonuclease Type 1) was added, the suspension mixed by inversion, incubated at 37° C. for 30 min. and centrifuged at 57,800×g as described above. The pellet was washed twice with buffer A and then resuspended in buffer C (30 mM HEPES buffer, pH 7.4 containing aprotinin (100 KIU/ml) to give a final protein concentration of 2 mg/ml.

The binding assay was performed, as described above for Test #1, except that the mixture was diluted to a final concentration of 1 µg protein/100µl of binding buffer.

3. Test for activity against endothelin-induced contraction of isolated rat thoracic arterial rings Compounds to be tested were prepared as 100 µM stocks. If necessary to effect dissolution, the compounds are first dissolved in a minimum amount of DMSO and diluted with 150 mM NaCl. Because DMSO can cause relaxation of the aortic ring, control solutions containing varying concentrations of DMSO were tested.

The thoracic portion of the adult rat aorta was excised, the endothelium abraded by gentle rubbing and then cut into 3 mm ring segments. Segments were suspended under a 2 g preload in a 10 ml organ bath filled with Krebs'-Henseleit solution saturated with a gas mixture of 95% $O_2$ and 5% $CO_2$ (118 mM NaCl, 4.7 mM KCl; 1.2 mM $MgSO_4$, 1.2 mM $KH_2PO_4$, 25 mM $NaHCO_3$, 2.5 mM $CaCl_2$, 10 mM D-glucose) gassed with 95% $O_2$/5% $CO_2$. Changes in tension were measured isometrically and recorded using a Grass Polygraph coupled to a force transducer.

Endothelin was added to the organ bath in a cumulatively increasing manner, and the effects of the test compounds on the concentration-response curve for endothelin-1 were examined. Compounds were added 15 min prior to the addition of endothelin-1.

4. Assay for identifying compounds that have antagonistic activity against $ET_B$ receptors Since endothelin-1 stimulates the release of prostacyclin from cultured bovine aortic endothelial cells, the cyclic peptides are screened for their ability to inhibit endothelin-1 induced prostacyclin release from such endothelial cells by measuring 6-keto $PGF_{1\alpha}$ substantially as described by Filep et al. (1991) *Biochem. Biophys. Res. Commun.* 177 171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and subcultured at least four times. The cells are then seeded in six-well plates in the same medium. Eight hours before the assay, after the cells reach confluence, the medium is replaced. The cells are then incubated with a) medium alone, b) medium containing endothelin-1 (10 nM), c) cyclic peptide alone, and d) cyclic peptide+endothelin-1 (10 nM).

After a 15 min incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Cyclic peptides which stimulate 6-keto $PGF_{1\alpha}$ release possess agonist activity and those which inhibit endothelinol 1 6-keto $PGF_{1\alpha}$ release possess antagonist activity.

B. Assay Results

1. The test results from binding assay #1 are set forth in Table 1:

TABLE 1

| TEST COMPOUND | $IC_{50}$ (μM) |
|---|---|
| (6) cyclo(D-Asp—Ala-D-Ala—Ala-D-Trp) | 7.3 |
| (7) cyclo(D-Tyr—Ala-D-Ala—Ala-D-Trp) | 52 |
| (2) cyclo(D-Tyr—Phe-D-His-β-Ala-D-Trp) | 100 |
| (9) cyclo(D-Asp—Ac₃c-D-Val—Leu-D-Trp) | 12 |

Membrane was prepared as described above for the $ET_A$ receptors. Using the membrane preparation diluted with binding buffer to a concentration of 1 μg/100 μl, the binding assay was performed as described above for the $ET_A$ receptors.

TABLE 2

| CYCLIC PEPTIDE | % Inhib 100 μM | |
|---|---|---|
| | $ET_A$ | $ET_B$ |
| D-Leu-L-Val-D-Pro-L-Asp-L-Trp | 96 | ND |
| D-Leu-L-Val-D-Pro-L-Tyr-L-Trp | 18 | ND |
| D-Leu-L-Val-D-Pro-L-Ser-L-Trp | 49.5 | ND |
| D-Leu-L-Val-D-Pro-L-Glu-L-Trp | 25 | 0 |
| D-Leu-L-Val-D-Ala-L-Asp-L-Trp | 26 | 15 |
| D-Leu-L-Val-L-Gly-L-Asp-L-Trp | 14 | 17 |
| D-Leu—Aib-L-Pro-L-Asp-L-Trp | 9.5 | 11 |
| D-Leu-L-Gly-L-Pro-L-Asp-L-Trp | 7.1 | 12 |
| D-Leu-D-Val-L-Pro-D-Asp-L-Trp | 80 | 2.2 |
| D-Leu-D-Val-L-Pro-D-Glu-L-Trp | 23 | 0 |

Peptides with the preferred backbone structure exhibit the best activity.

2. The test results from binding assay #2 are set forth in Table 3:

TABLE 3

| COMPOUND | $IC_{50}$ (μM) |
|---|---|
| (2) cyclo(D-Tyr—Phe-D-His-β-Ala-D-Trp) | 90 |
| (6) cyclo(D-Asp—Ala-D-Ala—Ala-D-Trp) | >100 |
| (7) cyclo(D-Tyr—Ala-D-Ala—Ala-D-Trp) | >100 |
| (9) cyclo(D-Asp—Ac₃c-D-Val—Leu-D-Trp) | 45 |

Cyclic peptide (9), cyclo(D-Asp-Ac₃c-D-Val-Leu-D-Trp), is, thus, an $ET_B$ antagonist.

3. Inhibition of Endothelin-1 induced contraction

Compounds (6) cyclo(D-Asp-Ala-D-Ala-Ala-D-Trp) and (7) cyclo (D-Tyr-Ala-D-Ala-Ala-D-Trp) showed no agonistic activity in the contraction assay. Compound (6) cyclo(D-Asp-Ala-D-Ala-Ala-D-Trp) at a concentration of 10 μM caused 75% inhibition of the contraction induced by 100 nM endothelin-1. Compound (7) cyclo(D-Tyr-Ala-D-Ala-Ala-D-Trp) at a concentration of 10 μM caused a 75% inhibition of the contraction induced by 100 nM endothelin-1.

Since modifications will be apparent to those of skill in this art, it is intended that this invention be limited only by the scope of the appended claims.

We claim:

1. A substantially pure peptide of formula (III):

cyclo($X^1$-$X^2$-$X^3$-$X^4$-L-Trp)     (III)

or a pharmaceutically acceptable salt thereof, wherein:

$X^1$ is D-Leu, D-Val, D-Ile, D-Ala, Gly, Aib, D-Nva, D-Nle or D-Alle; $X^2$ is L-Val, L-Ile, L-Leu, L-Ala, L-Gln, L-Gly, Aib, L-Nva, L-Nlle or L-Alle; $X^3$ is D-Pro, D-Hyp, D-Ala, D-Val, D-Ile, Gly, Aib, D-Nva, D-Nle or D-Alle; and $X^4$ is L-Asp, L-Glu, L-Tyr, L-Ser, L-Thr, L-Cys($O_3^H$) or L-Pen($O_3H$).

2. A peptide of claim 1, wherein $X^1$ is D-Leu, D-Val, D-Ile or D-Ala;

$X^2$ is L-Val, L-Ile, L-Leu or L-Ala;

$X^3$ is D-Pro, D-Ala, D-Val or D-Ile; and $X^4$ is L-Asp, L-Glu, L-Tyr or L-Ser.

3. The peptides of claim 2, wherein:

$X^1$ is D-Leu;

$X^2$ is L-Val, L-Ile, L-Leu or L-Ala;

$X^3$ is D-Pro, D-Ala, D-Val or D-Ile; and $X^4$ is L-Asp, L-Glu, L-Tyr or L-Ser.

4. The peptides of claim 3, wherein:

$X^1$ is D-Leu;

$X^2$ is L-Val;

$X^3$ is D-Pro, D-Ala, D-Val or D-Ile; and $X^4$ is L-Asp, L-Glu, L-Tyr or L-Ser.

5. A peptide of claim 4 selected from the group consisting of cyclo(D-Leu-L-Val-D-Pro-L-Tyr-L-Trp), cyclo(D-Leu-L-Val-D-Pro-L-Ser-L-Trp), cyclo(D-Leu-L-Val-D-Pro-L-Asp-L-Trp), cyclo(D-Leu-L-Val-D-Pro-L-Asp-L-Trp), cyclo(D-Leu-L-Val-D-Pro-L-Glu-L-Trp), cyclo(D-Leu-L-Val-D-Ala-L-Asp-L-Trp) and cyclo(D-Leu-L-Val-Gly-L-Asp-L-Trp).

6. A peptide of claim 5 that is D-Leu-L-Val-D-Pro-L-Asp-L-Trp or D-Leu-L-Val-D-Pro-L-Ser-L-Trp.

7. A pharmaceutical composition, comprising a peptide of claim 1, in a pharmaceutically acceptable vehicle.

8. The composition of claim 7, that is formulated for single dosage administration and that contains an amount of the peptide that is effective for ameliorating the symptoms of hypertension, cardiovascular disease, asthma, ophthalmologic disease, gastroenteric disease, renal failure, menstrual disorders, obstetric conditions, wounds, endotoxin shock, anaphylactic shock, or hemorrhagic shock.

9. A method for the treatment of endothelin-mediated diseases, comprising administering the composition of claim 8 to an individual wherein the effective amount is sufficient to ameliorate one or more symptoms of the endothelin-mediated disease.

10. An article of manufacture, comprising packaging material and a peptide of claim 1, contained within the packaging material, wherein the peptide is effective for antagonizing the effects of endothelin, ameliorating the symptoms of an endothelin-mediated disorder, or inhibiting the binding of an endothelin peptide to an ET receptor; and the packaging material includes a label that indicates that the peptide is used for antagonizing the effects of endothelin, inhibiting the binding of endothelin to an endothelin receptor or treating an endothelin-mediated disorder.

11. A method for inhibiting the binding of an endothelin peptide to endothelin$_A$ (ET$_A$) or endothelin$_B$ (ET$_B$) receptors, comprising contacting the receptors with an endothelin peptide and with one or more peptides of claim 1, wherein:
the contacting with the one or more peptides is effected prior to, simultaneously with or subsequent to contacting the receptors with the endothelin peptide.

12. A method for altering endothelin receptor-mediated activity, comprising contacting endothelin receptors with one or more peptides of claim 1.

13. A pharmaceutical composition, comprising a peptide of claim 2 in a pharmaceutically acceptable vehicle.

14. The composition of claim 13, that is formulated for single dosage administration and that contains an amount of the peptide that is effective for ameliorating the symptoms of hypertension, cardiovascular disease, asthma, ophthalmologic disease, gastroenteric disease, renal failure, menstrual disorders, obstetric conditions, wounds, endotoxin shock, anaphylactic shock, or hemorrhagic shock.

15. A method for the treatment of endothelin-mediated diseases, comprising administering the composition of claim 14 to an individual wherein the effective amount is sufficient to ameliorate one or more symptoms of the endothelin-mediated disease.

16. An article of manufacture, comprising packaging material and a peptide of claim 2 contained within the packaging material, wherein the peptide is effective for antagonizing the effects of endothelin, ameliorating the symptoms of an endothelin-mediated disorder, or inhibiting the binding of an endothelin peptide to an ET receptor; and the packaging material includes a label that indicates that the peptide is used for antagonizing the effects of endothelin, inhibiting the binding of endothelin to an endothelin receptor or treating an endothelin-mediated disorder.

17. A method for inhibiting the binding of an endothelin peptide to endothelin$_A$ (ET$_A$) or endothelin$_B$ (ET$_B$) receptors, comprising contacting the receptors with an endothelin peptide and with one or more peptides of claim 2, wherein:
the contacting with the one or more peptides is effected prior to, simultaneously with or subsequent to contacting the receptors with the endothelin peptide.

18. A method for altering endothelin receptor-mediated activity, comprising contacting endothelin receptors with one or more peptides of claim 2.

19. A pharmaceutical composition, comprising a peptide of claim 3 in a pharmaceutically acceptable vehicle.

20. The composition of claim 18, that is formulated for single dosage administration and that contains an amount of the peptide that is effective for ameliorating the symptoms of hypertension, cardiovascular disease, asthma, ophthalmologic disease, gastroenteric disease, renal failure, menstrual disorders, obstetric conditions, wounds, endotoxin shock, anaphylactic shock, or hemorrhagic shock.

21. A method for the treatment of endothelin-mediated diseases, comprising administering the composition of claim 20 to an individual wherein the effective amount is sufficient to ameliorate one or more symptoms of the endothelin-mediated disease.

22. An article of manufacture, comprising packaging material and a peptide of claim 3 contained within the packaging material, wherein the peptide is effective for antagonizing the effects of endothelin, ameliorating the symptoms of an endothelin-mediated disorder, or inhibiting the binding of an endothelin peptide to an ET receptor; and the packaging material includes a label that indicates that the peptide is used for antagonizing the effects of endothelin, inhibiting the binding of endothelin to an endothelin receptor or treating an endothelin-mediated disorder.

23. A method for inhibiting the binding of an endothelin peptide to endothelin$_A$ (ET$_A$) or endothelin$_B$ (ET$_B$) receptors, comprising contacting the receptors with an endothelin peptide and with one or more peptides of claim 3, wherein:
the contacting with one or more peptides is effected prior to, simultaneously with or subsequent to contacting the receptors with the endothelin peptide.

24. A method for altering endothelin receptor-mediated activity, comprising contacting endothelin receptors with one or more peptides of claim 3.

25. A pharmaceutical composition, comprising a peptide of claim 4 in a pharmaceutically acceptable vehicle.

26. The composition of claim 25, that is formulated for single dosage administration and that contains an amount of the peptide that is effective for ameliorating the symptoms of hypertension, cardiovascular disease, asthma, ophthalmologic disease, gastroenteric disease, renal failure, menstrual disorders, obstetric conditions, wounds, endotoxin shock, anaphylactic shock, or hemorrhagic shock.

27. A method for the treatment of endothelin-mediated diseases, comprising administering the composition of claim 26 to an individual wherein the effective amount is sufficient to ameliorate one or more symptoms of the endothelin-mediated disease.

28. An article of manufacture, comprising packaging material and a peptide of claim 4 contained within the packaging material, wherein the peptide is effective for antagonizing the effects of endothelin, ameliorating the symptoms of an endothelin-mediated disorder, or inhibiting the binding of an endothelin peptide to an ET receptor; and the packaging material includes a label that indicates that the peptide is used for antagonizing the effects of endothelin, inhibiting the binding of endothelin to an endothelin receptor or treating an endothelin-mediated disorder.

29. A method for inhibiting the binding of an endothelin peptide to endothelin$_A$(ET$_A$) or endothelin$_B$ (ET$_B$) receptors, comprising contacting the receptors with an endothelin peptide and with one or more peptides of claim 4, wherein:
the contacting with the one or more peptides is effected prior to, simultaneously with or subsequent to contacting the receptors with the endothelin peptide.

30. A method for altering endothelin receptor-mediated activity, comprising contacting endothelin receptors with one or more peptides of claim 4.

31. A pharmaceutical composition, comprising a peptide of claim 5 in a pharmaceutically acceptable vehicle.

32. The composition of claim 31, that is formulated for single dosage administration and that contains an amount of the peptide that is effective for ameliorating the symptoms of hypertension, cardiovascular disease, asthma, ophthalmologic disease, gastroenteric disease, renal failure, menstrual disorders, obstetric conditions, wounds, endotoxin shock, anaphylactic shock, or hemorrhagic shock.

33. A method for the treatment of endothelin-mediated diseases, comprising administering the composition of claim 32 to an individual wherein the effective amount is sufficient to ameliorate one or more symptoms of the endothelin-mediated disease.

34. An article of manufacture, comprising packaging material and a peptide of claim 5 contained within the packaging material, wherein the peptide is effective for antagonizing the effects of endothelin, ameliorating the symptoms of an endothelin-mediated disorder, or inhibiting the binding of an endothelin peptide to an ET receptor; and the packaging material includes a label that indicates that the peptide is used for antagonizing the effects of endothelin, inhibiting the binding of endothelin to an endothelin receptor or treating an endothelin-mediated disorder.

35. A method for inhibiting the binding of an endothelin peptide to endothelin$_A$ (ET$_A$) or endothelin$_B$ (ET$_B$) receptors, comprising contacting the receptors with an endothelin peptide and with one or more peptides of claim 5, wherein:

the contacting with the one or more peptides is effected prior to, simultaneously with or subsequent to contacting the receptors with the endothelin peptide.

36. A method for altering endothelin receptor-mediated activity, comprising contacting endothelin receptors with one or more peptides of claim 5.

37. A pharmaceutical composition, comprising a peptide of claim 6 in a pharmaceutically acceptable vehicle.

38. The composition of claim 37, that is formulated for single dosage administration and that contains an amount of the peptide that is effective for ameliorating the symptoms of hypertension, cardiovascular disease, asthma, ophthalmologic disease, gastroenteric disease, renal failure, menstrual disorders, obstetric conditions, wounds, endotoxin shock, anaphylactic shock, or hemorrhagic shock.

39. A method for the treatment of endothelin-mediated diseases, comprising administering the composition of claim 37 to an individual wherein the effective amount is sufficient to ameliorate one or more symptoms of the endothelin-mediated disease.

40. An article of manufacture, comprising packaging material and a peptide of claim 6 contained within the packaging material, wherein the peptide is effective for antagonizing the effects of endothelin, ameliorating the symptoms of an endothelin-mediated disorder, or inhibiting the binding of an endothelin peptide to an ET receptor; and the packaging material includes a label that indicates that the peptide is used for antagonizing the effects of endothelin, inhibiting the binding of endothelin to an endothelin receptor or treating an endothelin-mediated disorder.

41. A method for inhibiting the binding of an endothelin peptide to endothelin$_A$ (ET$_A$) or endothelin$_B$ (ET$_B$) receptors, comprising contacting the receptors with an endothelin peptide and with one or more peptides of claim 6, wherein:

the contacting with the one or more peptides is effected prior to, simultaneously with or subsequent to contacting the receptors with the endothelin peptide.

* * * * *

UNITED STATES PATENT AND TRADEMARK OFFICE

CERTIFICATE OF CORRECTION

| | |
|---|---|
| PATENT NO.: | 5,736,509 |
| DATED: | April 7, 1998 |
| INVENTOR(S): | BALAJI, Vitukudi Narayanaiyengar; and CHAN, Ming Fai |

It is certified that error appears in the above-identified patent and that said Letters Patent is hereby corrected as shown below:

On the title page, item [63], in column 1:
IN THE RELATED U.S. APPLICATIONS:
    at line 1, insert —abandoned,— after "April 5, 1994,".
IN THE REFERENCES CITED:
    Please add the following U.S. Patent documents:
    —5,430,022 07/04/95 Hemmi et al. 514/18—; and
    —5,439,887 08/08/95 Hamon et al. 514/13—.
IN THE SPECIFICATION:
    at column 1, lines 4-10,
"This application is a Continuation-in-part of U.S. application Ser. No. 08/223,513, filed Apr. 5, 1994, now abandoned, and also a Continuation-in-part of U.S. application Ser. No. 07/900,623, filed Jun. 18, 1992, now abandoned, which is a Continuation-in-part of U.S. application Ser. No. 07/628,111, filed Dec. 14, 1990, now U.S. Pat. No. 5,331,573." should read
    —This application is a continuation-in-part of U.S. application Ser. No. 07/900,623 to Ming Fai Chan and Vitukudi N. Balaji, filed Jun. 18, 1992, entitled "CYCLIC PEPTIDE SURFACE FEATURE MIMICS OF ENDOTHELIN", now abandoned, which is a continuation-in-part of U.S. Application Serial No. 07/628,111, filed December 14, 1990, now U.S. Patent No. 5,331,573, to Vitukudi N. Balaji and Chandra U. Singh, entitled "METHOD OF DESIGN OF COMPOUNDS THAT MIMIC CONFORMATIONAL FEATURES OF SELECTED PEPTIDES". This application is also a Continuation-in-part of U.S. application Ser. No. 08/427,987 to Vitukudi N. Balaji and Chandra U. Singh, filed April 24, 1995, entitled "A METHOD OF RATIONAL DRUG DESIGN BASED ON *AB INITIO* COMPUTER SIMULATION OF CONFORMATIONAL FEATURES OF PEPTIDES", now U.S. Pat. No. 5,579,250, which is a Continuation of U.S. application Ser. No. 08/223,513 to Vitukudi N. Balaji and Chandra U. Singh, filed Apr. 5, 1994, entitled "RATIONAL DESIGN OF COMPOUNDS THAT MIMIC CONFORMATIONAL FEATURES OF SELECTED PEPTIDES", now abandoned.
    U.S. Application Serial Nos. 08/223,513, 08/427,987, 07/900,623 and 07/628,111, and U.S. Patent Nos. 5,331,573 and 5,579,250 each are incorporated herein in its entirety by reference thereto.—;

UNITED STATES PATENT AND TRADEMARK OFFICE

CERTIFICATE OF CORRECTION

PATENT NO.: 5,736,509

DATED: April 7, 1998

INVENTOR(S): BALAJI, Vitukudi Narayanaiyengar; and CHAN, Ming Fai

It is certified that error appears in the above-identified patent and that said Letters Patent is hereby corrected as
shown below:

at column 2, line 41, "phosphoinoside" should read —phosphoinositide—;
at column 3, line 29, "MCMurdo" should read —McMurdo—;
at column 3, line 67, "anthraquinone," should read —anthraquinone—;
at column 4, line 48, "artherosclerois" should read —atherosclerosis—;
at column 11, line 37, "herein" should read —herein,—;
at column 15, line 7, "shirking" should read —shrinking—;
at column 18, line 18, "Castiglinone" should read —de Castiglione—;
at column 23, lines 45-46, "pharmaceuitically" should read —pharmaceutically—;
at column 24, line 65, "aleprotected" should read —deprotected—;
at column 34, line 19, "Vield" should read —yield—;
at column 34, line 43, "Steward" should read —Stewart—; and
at column 34, line 56, "ml." should read —ml—.

IN THE CLAIMS:

at column 38, line 35, "L-Cys($O_3^H$)" should read —L-Cys($O_3$H)—.

Signed and Sealed this

Seventeenth Day of November, 1998

Attest:

BRUCE LEHMAN

Attesting Officer

Commissioner of Patents and Trademarks